United States Patent
Abe et al.

(10) Patent No.: US 10,514,432 B2
(45) Date of Patent: Dec. 24, 2019

(54) MAGNETIC FIELD ADJUSTING METHOD

(71) Applicant: HITACHI, LTD., Tokyo (JP)

(72) Inventors: Mitsushi Abe, Tokyo (JP); Kenji Sakakibara, Tokyo (JP); Takuya Fujikawa, Tokyo (JP); Hikaru Hanada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 350 days.

(21) Appl. No.: 15/549,826

(22) PCT Filed: Feb. 19, 2016

(86) PCT No.: PCT/JP2016/054880
§ 371 (c)(1),
(2) Date: Aug. 9, 2017

(87) PCT Pub. No.: WO2016/133205
PCT Pub. Date: Aug. 25, 2016

(65) Prior Publication Data
US 2018/0031650 A1    Feb. 1, 2018

(30) Foreign Application Priority Data
Feb. 20, 2015 (JP) .................... 2015-031255

(51) Int. Cl.
*G01R 33/3875* (2006.01)
*G01R 33/3873* (2006.01)
(Continued)

(52) U.S. Cl.
CPC ..... *G01R 33/3875* (2013.01); *G01R 33/3873* (2013.01); *G01N 24/08* (2013.01); *G01R 33/20* (2013.01)

(58) Field of Classification Search
CPC ........ G01R 33/00; G01R 33/20; G01R 33/28; G01R 33/32; G01R 33/323; G01R 33/326;
(Continued)

(56) References Cited

U.S. PATENT DOCUMENTS 5,371,465 A * 12/1994 Onodera ............ G01R 33/3875
324/307
2011/0089943 A1    4/2011 Abe et al.
(Continued)

FOREIGN PATENT DOCUMENTS

| JP | 2011110065 A | 6/2011 |
| JP | 4902787 B | 1/2012 |

(Continued)

OTHER PUBLICATIONS

International Search Report of PCT/JP2016/054880 dated May 29, 2016.

*Primary Examiner* — Hoai-An D. Nguyen
(74) *Attorney, Agent, or Firm* — Mattingly & Malur, PC

(57) ABSTRACT

In the present invention, a current plane which is virtually disposed and surrounds a measurement position is assumed from magnetic field measurement values, and a current distribution (or magnetic moment distribution) which mimics a measured magnetic field is reproduced with current potentials. This is used to perform shimming calculation by a truncated singular value decomposition method with discrete shim trays that are actually used and ideal virtual continuous shim trays to carry out shimming under conditions for shimming having a uniformity that is close to ideal shimming.

22 Claims, 15 Drawing Sheets

(51) Int. Cl.
*G01N 24/08* (2006.01)
*G01R 33/20* (2006.01)

(58) Field of Classification Search
CPC .. G01R 33/34; G01R 33/34023; G01R 33/38; G01R 33/387; G01R 33/3873; G01R 33/3875; G01R 33/44; G01R 33/441; G01R 33/565; G01R 33/5659; G01R 33/56572; G01N 24/00; G01N 24/08; G01N 24/084; G01N 24/10
USPC .......................................... 324/300, 607, 309
See application file for complete search history.

(56) References Cited

U.S. PATENT DOCUMENTS

| | | |
|---|---|---|
| 2012/0268119 A1 | 10/2012 | Abe et al. |
| 2014/0009152 A1 | 1/2014 | Sakakibara |
| 2017/0090000 A1* | 3/2017 | Lin ................... G01R 33/3607 |
| 2018/0003784 A1* | 1/2018 | Hanada ................. A61B 5/055 |

FOREIGN PATENT DOCUMENTS

| | | |
|---|---|---|
| WO | 2012132911 A1 | 4/2012 |
| WO | 2015005109 A1 | 1/2015 |

\* cited by examiner

[Fig. 1]
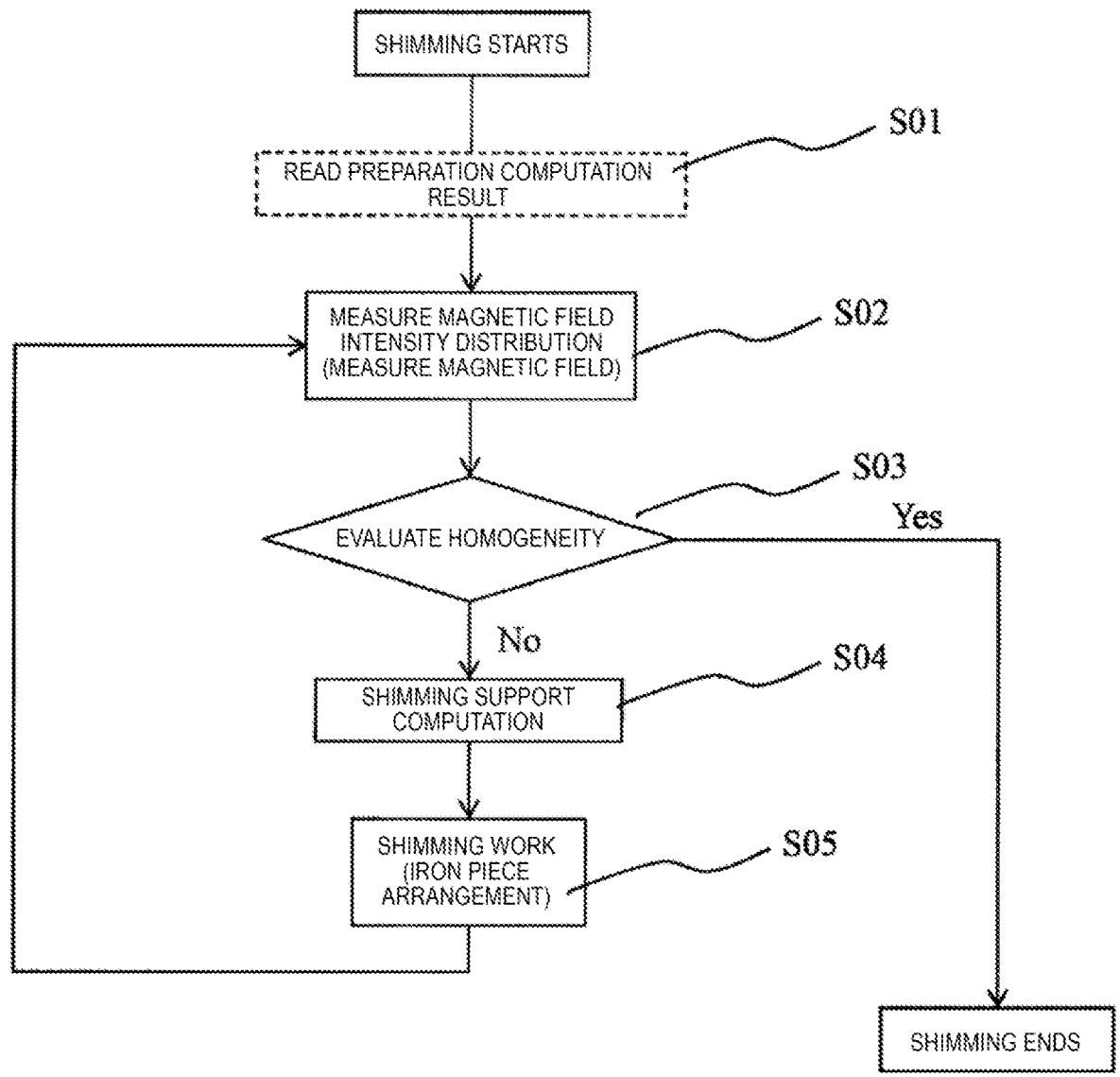

[Fig. 4]
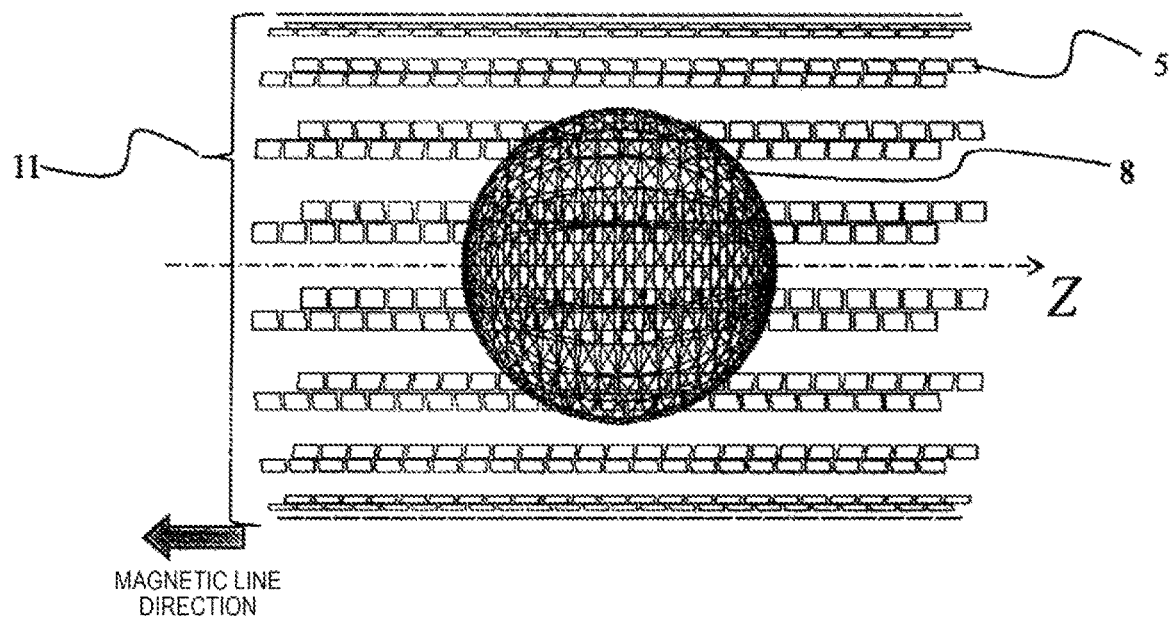
MAGNETIC LINE DIRECTION
[Fig. 5]
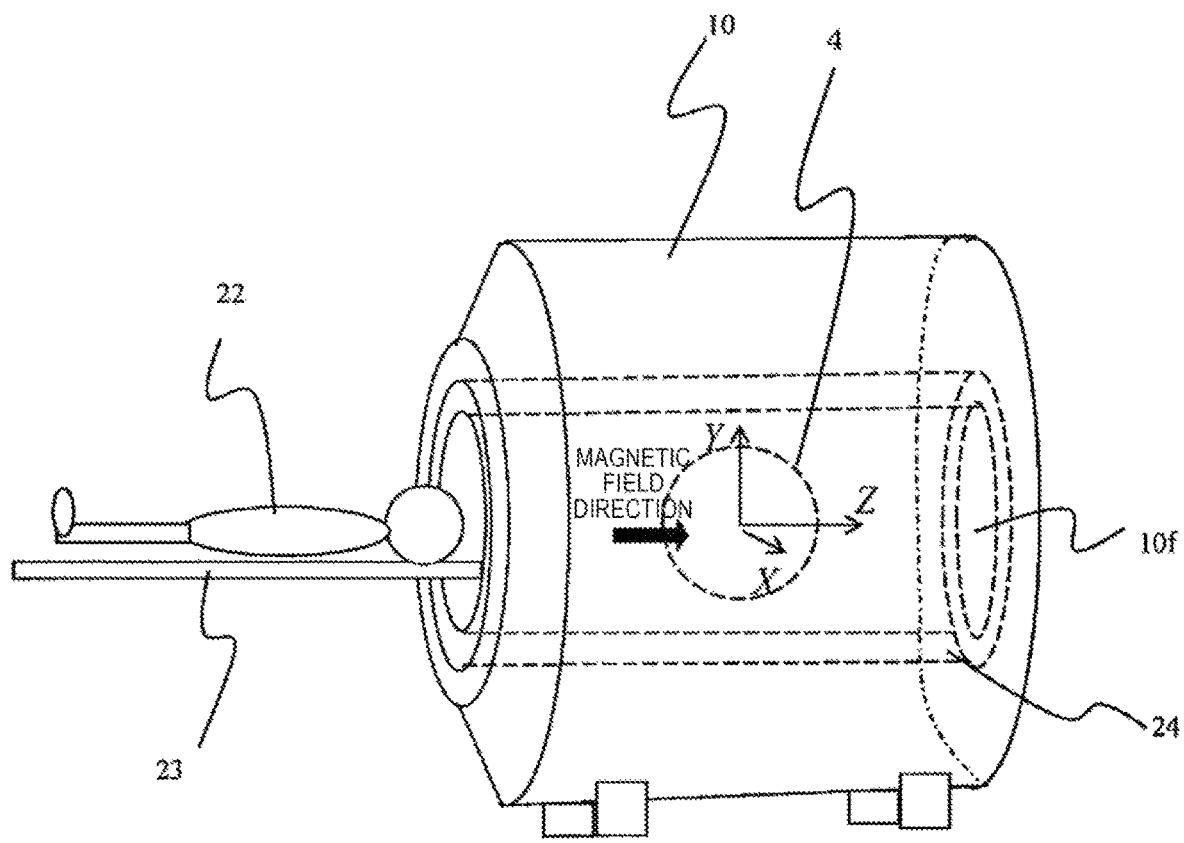

[Fig. 6]
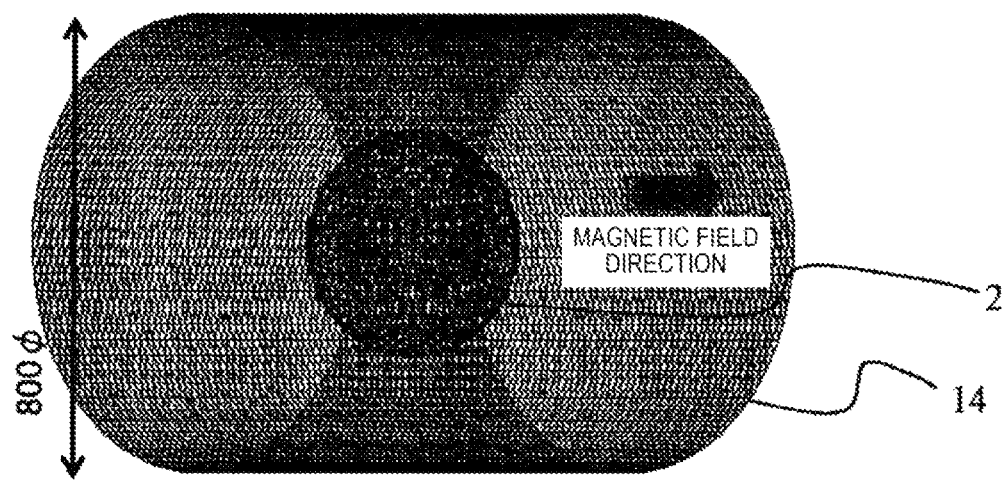
[Fig. 7]
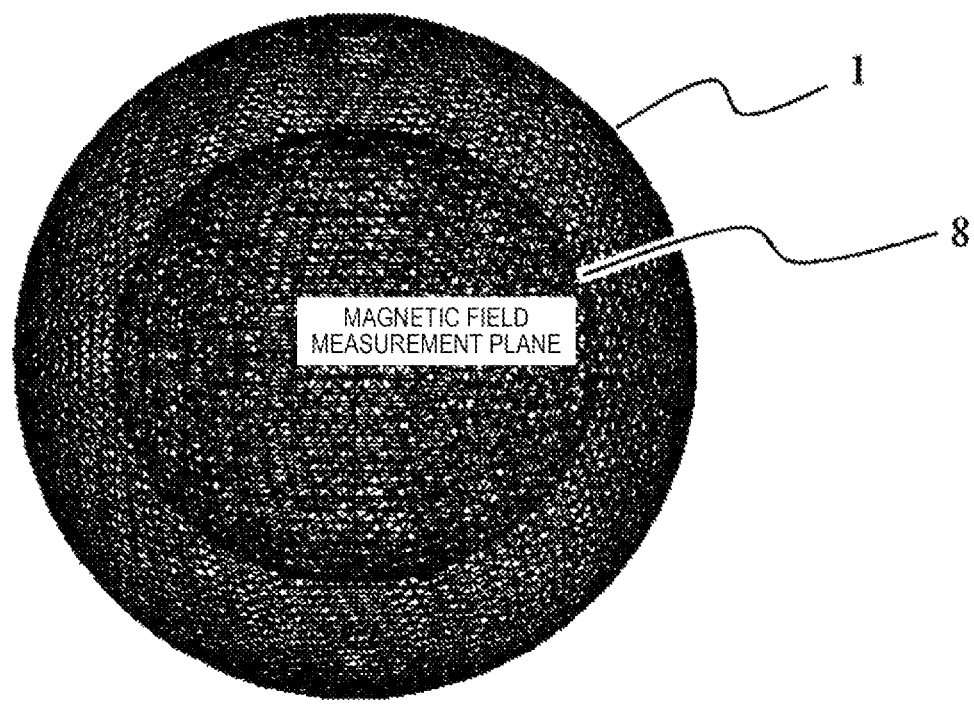

[Fig. 8]
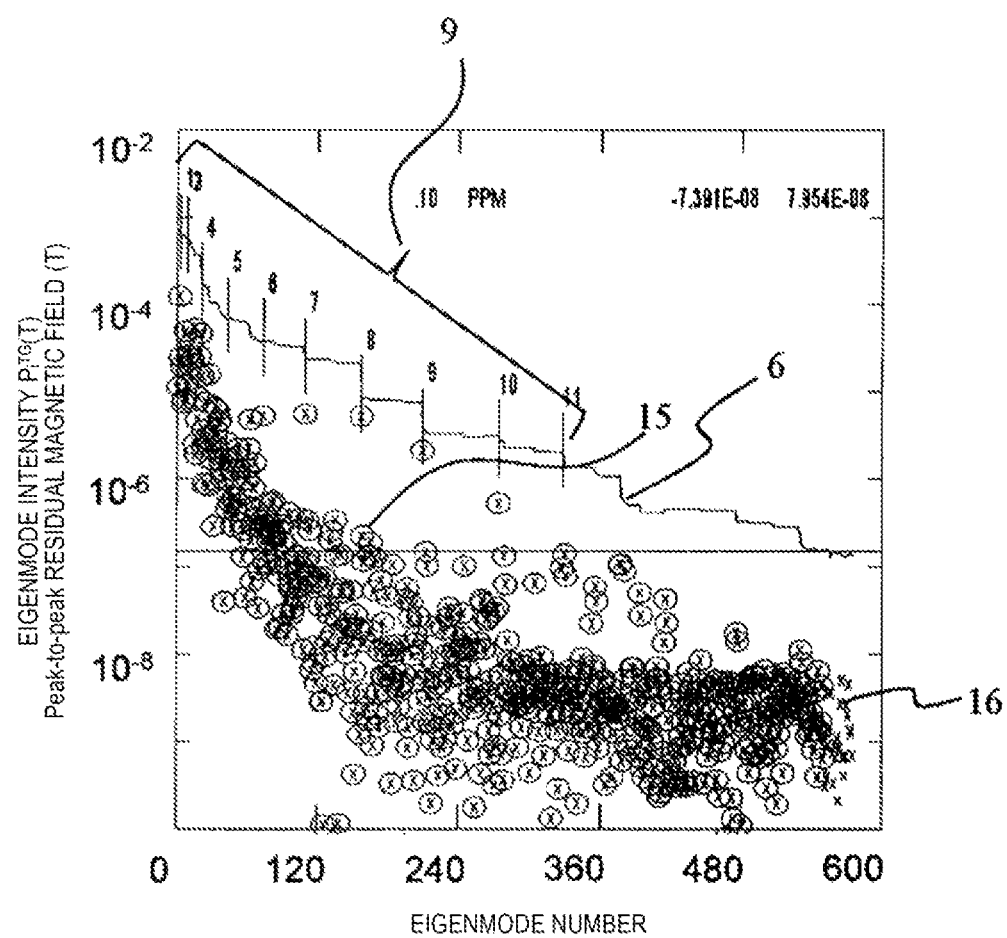

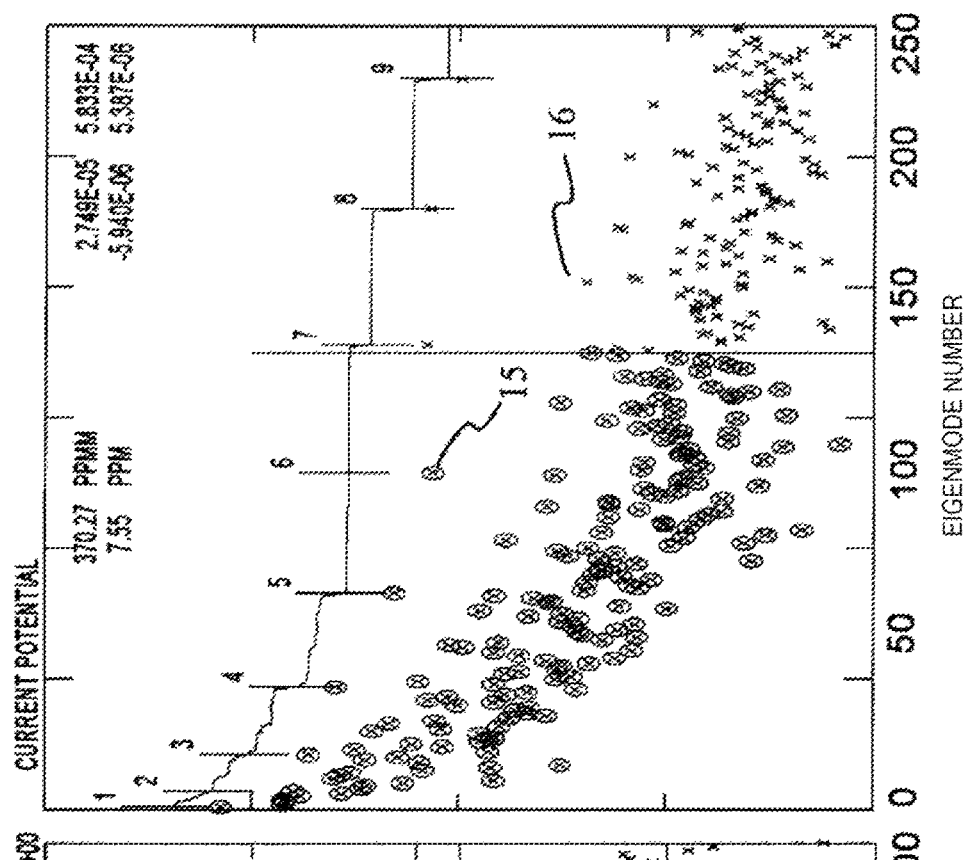
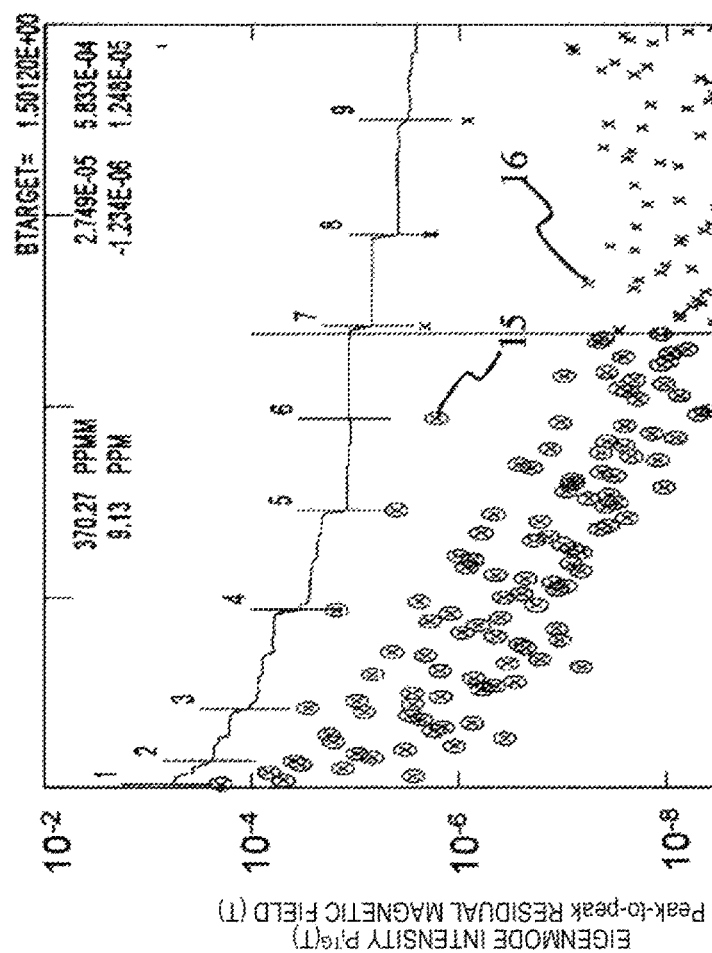
Fig. 10A
Fig. 10B

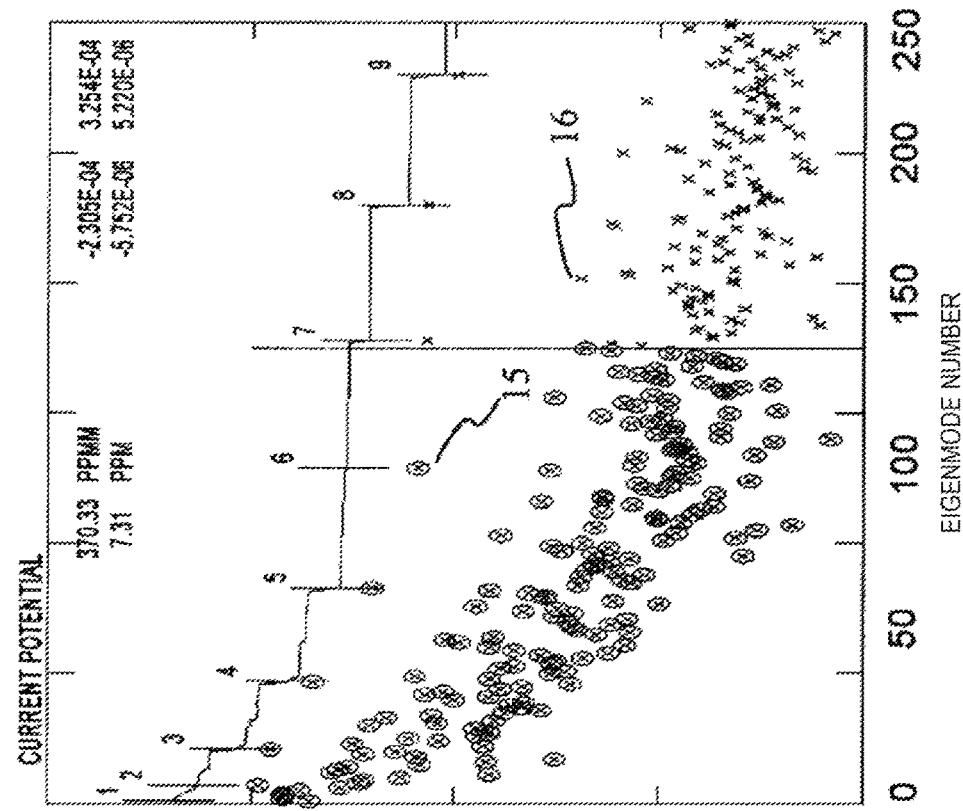
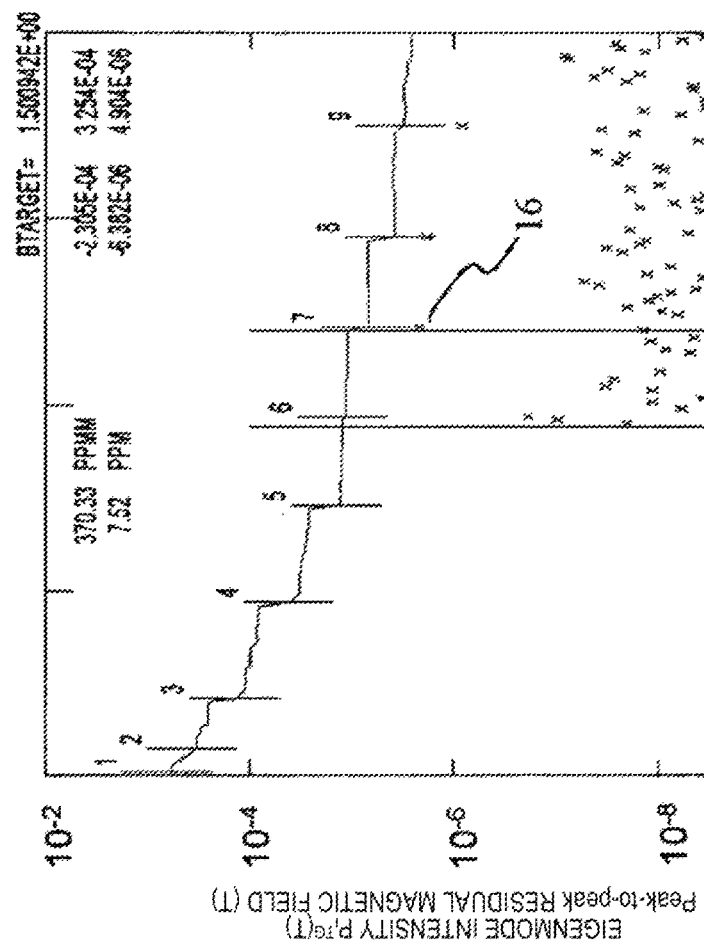
Fig. 11A
Fig. 11B

[Fig. 12]
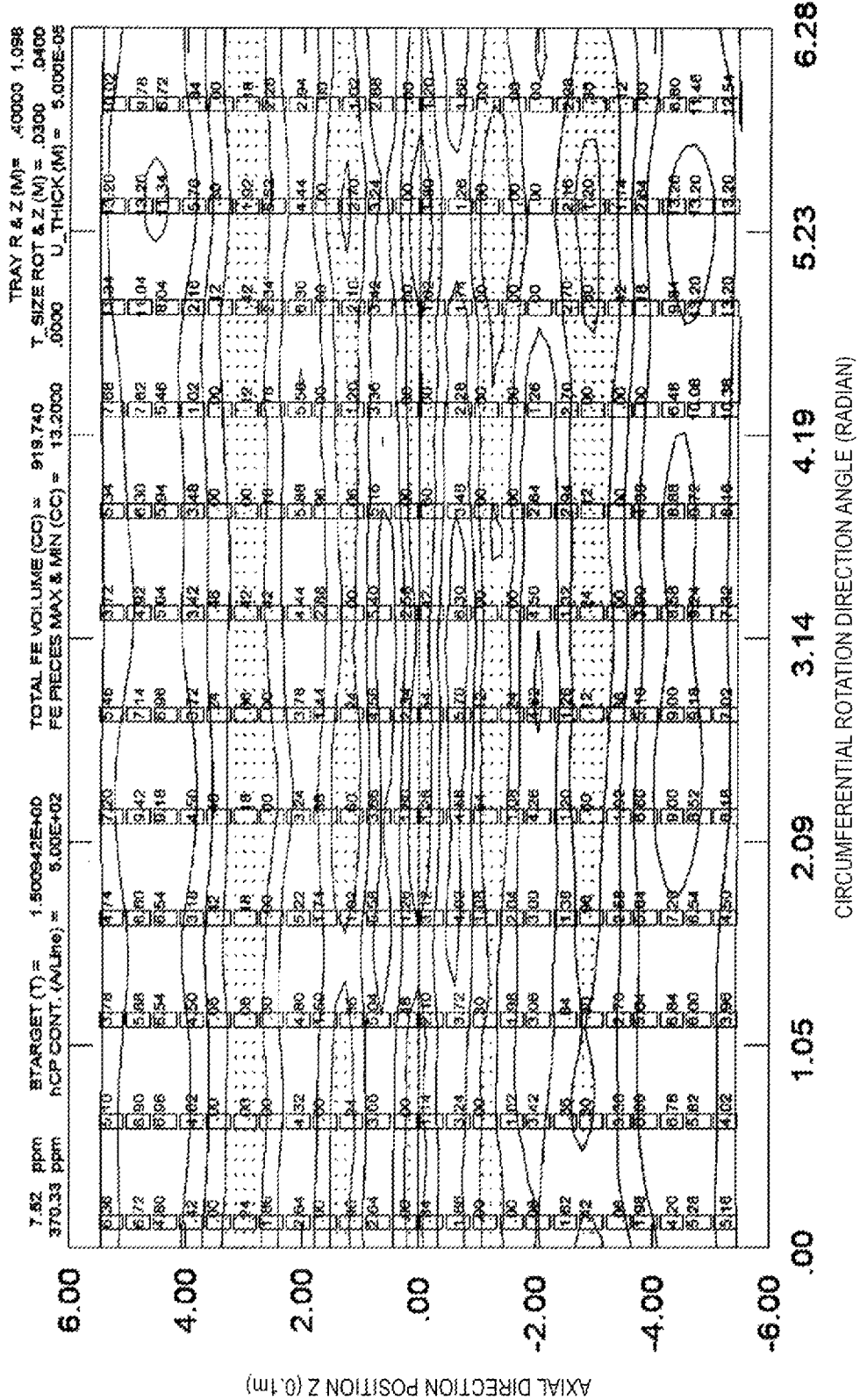

[Fig. 13]
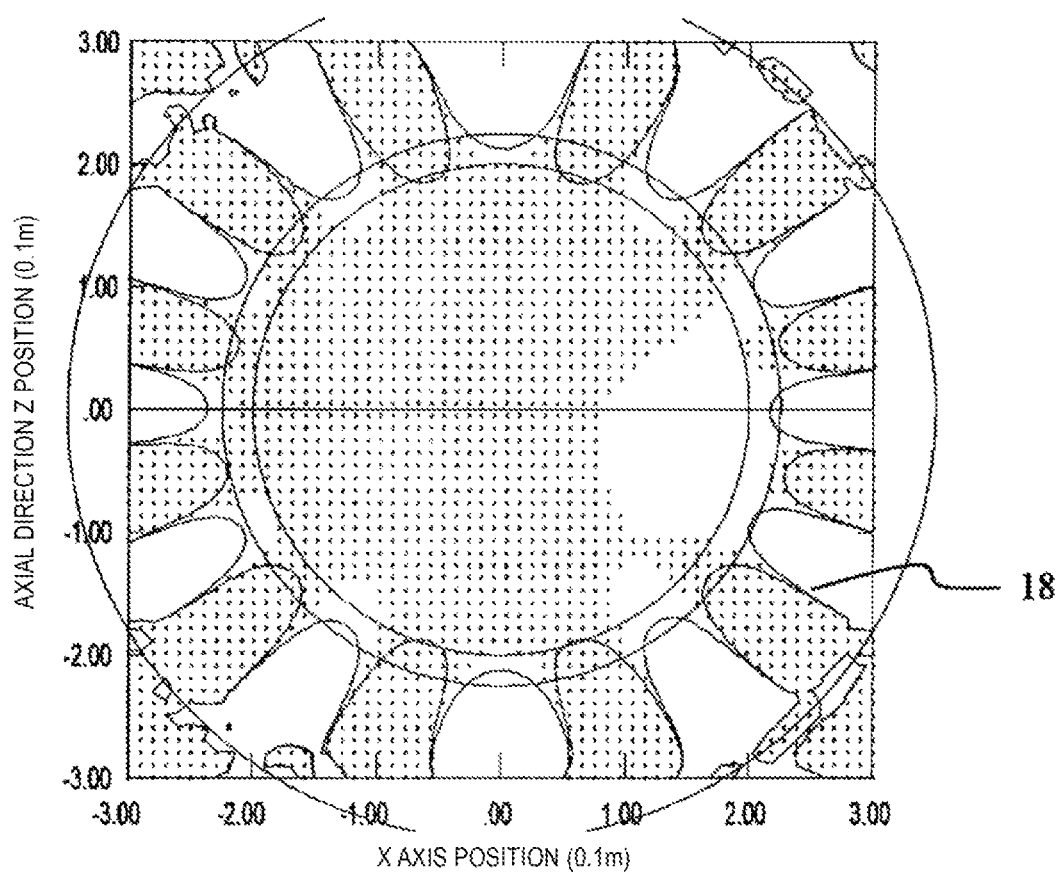

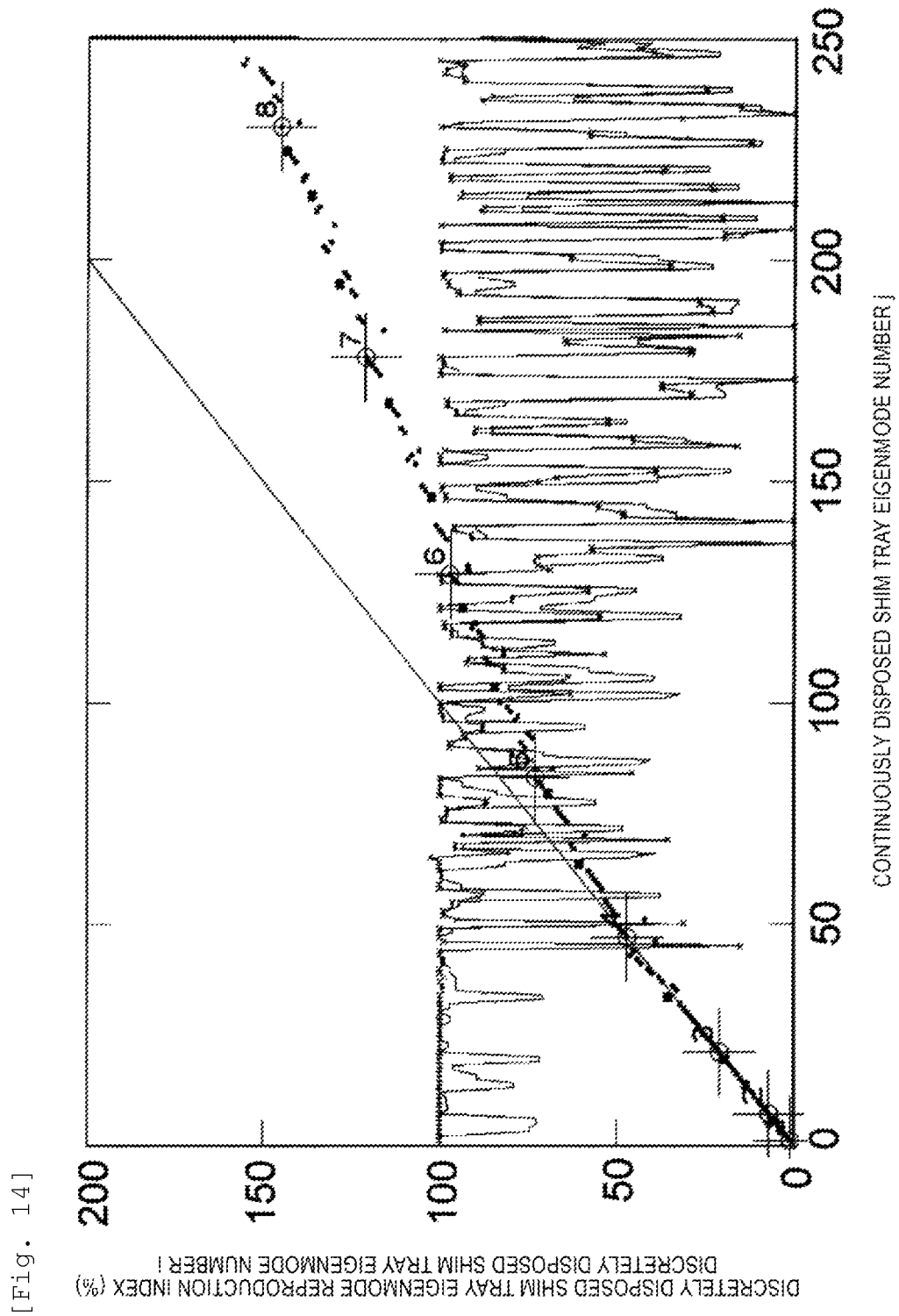
[Fig. 14]

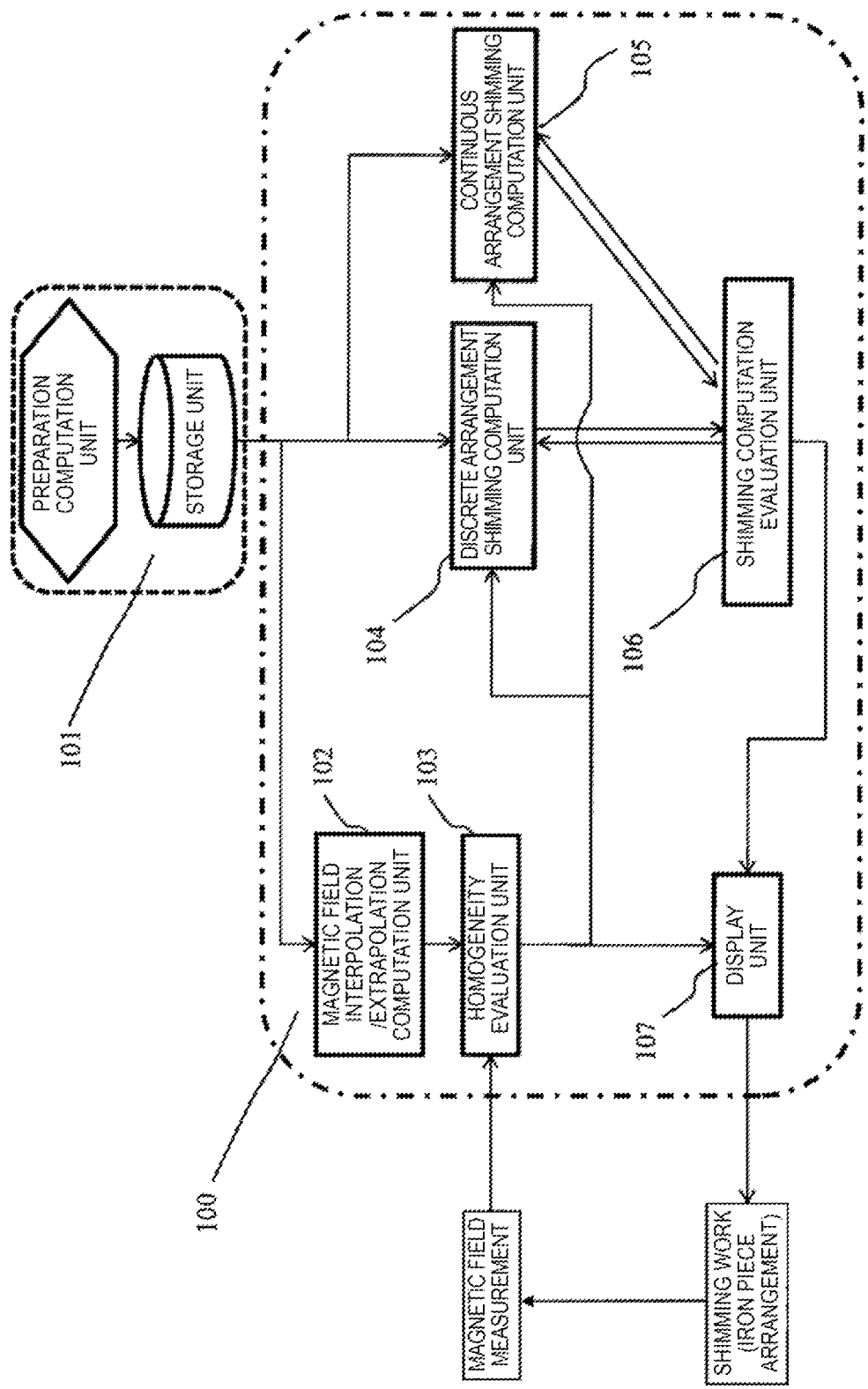
[Fig. 15]

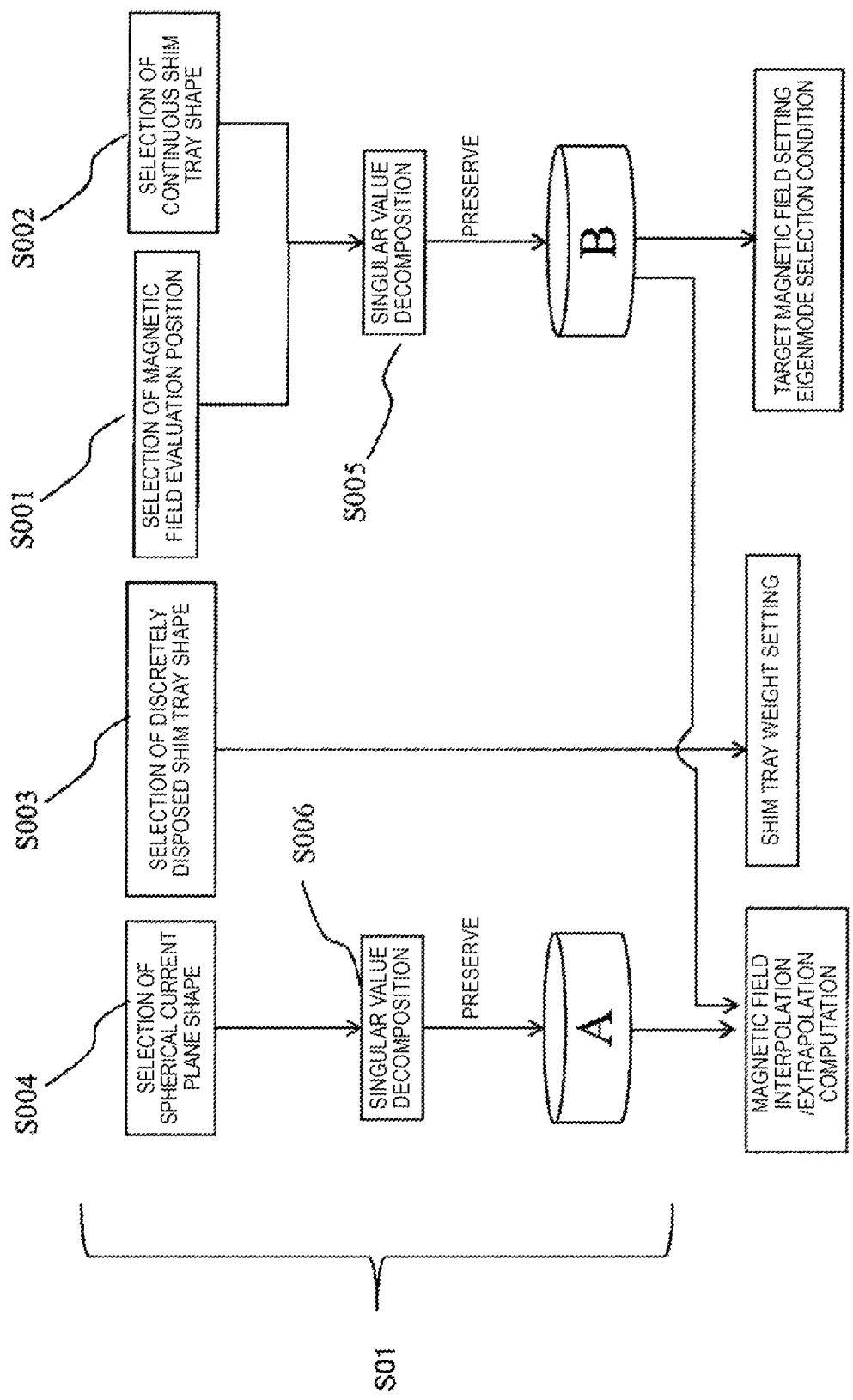
[Fig. 16]

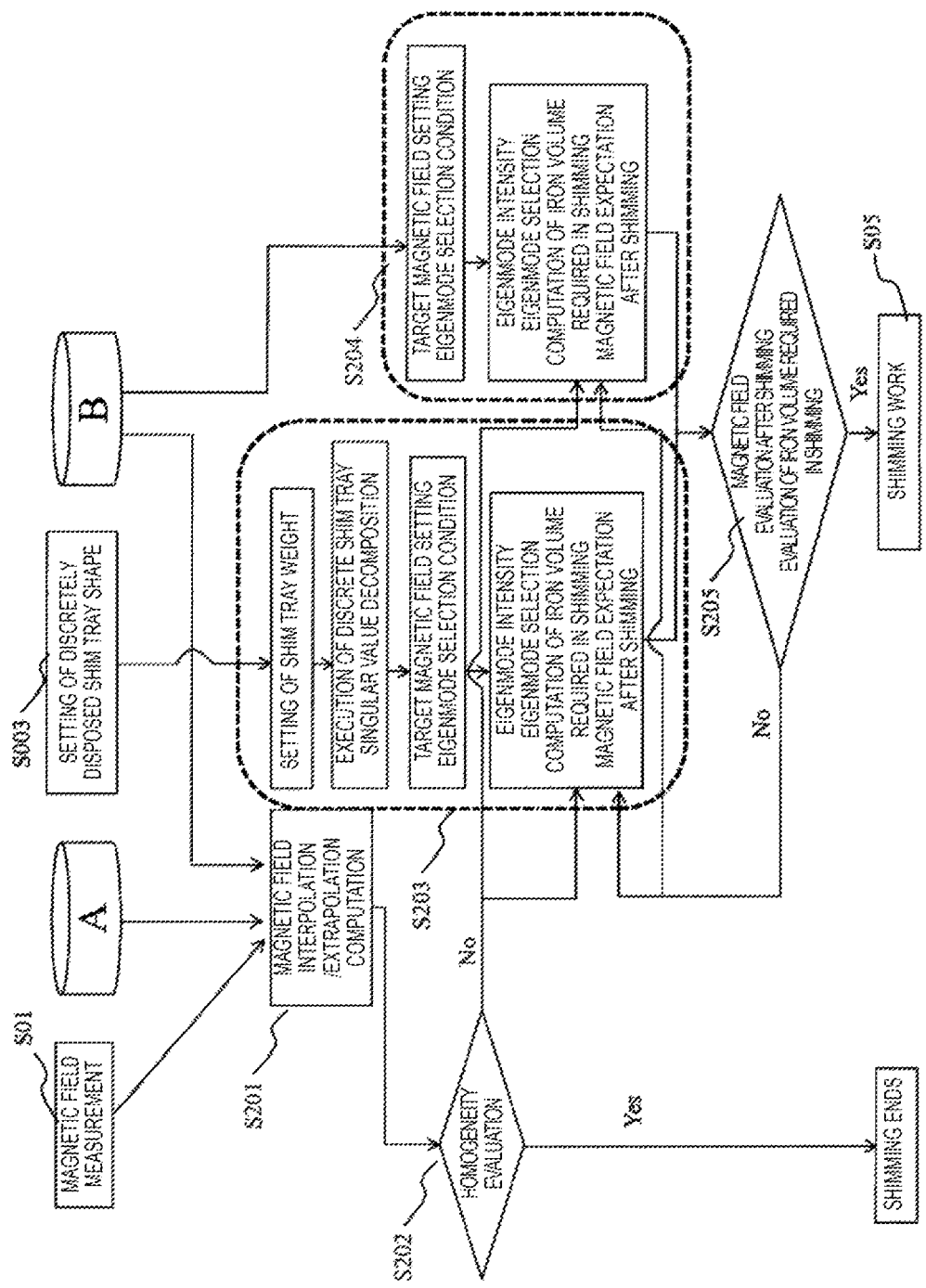
[Fig. 17]

MAGNETIC FIELD ADJUSTING METHOD

TECHNICAL FIELD

The present invention provides a method of adjusting a magnetic field to a desired magnetic intensity distribution in a magnet apparatus in which a magnetic body such as a coil or iron is disposed and a magnetic field is generated, such as a nuclear magnetic resonance tomographic apparatus (MRI) used for medical diagnosis.

BACKGROUND ART

In diagnosis using a nuclear magnetic resonance, the required accuracy in magnetic intensity of a magnet system is such that variation of one millionth in magnetic intensity is considered to be a problem since the magnetic intensity corresponds to a diagnosis location. There are three types of magnetic fields in MRI apparatuses. That is:

(1) A magnetic field that is a constant in time base and uniform in space, and has an intensity of generally more than 0.1 to several teslas and a variation range of about several ppm within a space for imaging (a space of a sphere or an ellipsoid with a diameter of 30 to 40 cm);

(2) A magnetic field varying with a time constant of about one second or shorter and inclined in a space; and (3) A magnetic field caused by a high frequency wave having a frequency (several MHz or higher) corresponding to the nuclear magnetic resonance.

The present invention focuses on a static magnetic field of (1). This magnetic field is required to have constant intensity in time base and spatially have homogeneity in the intensity with extremely high accuracy in a region where tomographic imaging of a human body is performed, especially, in a case of a magnetic resonance imaging apparatus.

The high accuracy mentioned here indicates the accuracy of a residual magnetic field with an order of one millionth, such as ±1.5 ppm, in an imaging space FOV (Field of View) with a diameter of, for example, 40 cm. A magnetic field distribution of which homogeneity is required to be extremely high is realized by adjusting a magnetic field after production and excitation of a magnet with high accuracy.

Generally, the magnitude of an error magnetic field due to a production error is 1000 times or more greater than the magnitude of the permissible error magnetic field demanded for a uniform magnetic field. Therefore, magnetic field adjustment (shimming) required when the apparatus is installed after production requires a magnetic field adjustment apparatus and a method with extremely high accuracy since an error magnetic field is reduced from hundreds ppm to several ppm.

As a method of the related art, PTL 1 discloses that arrangement of magnetic moment using singular value decomposition is computed, and shimming is performed by using a result thereof. In PTL 1, a distribution of magnetic moment or an iron piece volume is computed by using truncated singular value decomposition and a current potential, and iron piece arrangement magnetic field measurement work is performed on the basis of a result thereof.

PTL 1 discloses an example in which magnetic bodies for shimming are continuously disposed. FIGS. 2A and 2B illustrate a system of shimming computation and a computation result disclosed in PTL 1. In a shimming method of the related art in FIGS. 2A and 2B, FIG. 2A is a figure illustrating a shimming computation system, and FIG. 2B is a figure for explaining an eigenmode intensity and an eigenmode selected for shimming. According to PTL 1, a shimming iron volume is calculated in numerical values for each region on a continuous plane according to a contour line, but the shimming iron volume is not a discrete volume in which a standardized unit iron volume is reflected.

However, shimming is often to be performed after a volume and a position of iron to be disposed are standardized, that is, a volume and a position of iron to be disposed are discretized from the viewpoint of productivity and workability, depending on models. The term "discrete" mentioned here indicates two meanings such as spatially being discretized, and the minimum unit being present even in a shimming iron volume.

As an approach regarding such discrete arrangement, for example, there is PTL 2.

CITATION LIST

Patent Literature

PTL 1: Japanese Patent No. 49702787
PTL 2: JP-A-09-238917

Non-Patent Literature

NPL 1: M. ABE, T. NAKAYAMA, S. OKAMURA, K. MATSUOKA, "A new technique to optimize coil winding path for the arbitrarily distributed magnetic field and application to a helical confinement system", Phys. Plasmas. Vol. 10, No. 4 (2003), 1022

NPL 2: M. Abe, K. Shibata, "Consideration on Current and Coil Block Placements with Good Homogeneity for MRI Magnets using Truncated SVD", IEEE Trans. Magn., vol. 49, no. 6, pp. 2873 to 2880, June. 201

SUMMARY OF INVENTION

Technical Problem

However, PTL 2 does not disclose comparison with a case where iron pieces are ideally disposed, and thus homogeneity which can be reached in principle is not clear. Thus, it is hard to select shimming conditions, that is, to evaluate homogeneity which is realized as a result of performing shimming.

Therefore, the present invention describes a shimming method, a computation method performed by a computer supporting the work, and screen display of a result thereof, and provides a shimming method and a magnet using the same, and a magnetic resonance imaging apparatus, in order to solve the above-described problems.

Solution to Problem

In order to solve the above-described problem, the present invention may employ various embodiments, as an example thereof, there is provided "a magnetic field adjusting method of correcting a magnetic field distribution generated by a magnet apparatus in a magnetic field correction mechanism in a magnet system including the magnet apparatus forming a uniform magnetic field intensity distribution in a predetermined space and the magnetic field correction mechanism correcting the magnetic field intensity distribution, the method including a first step of measuring a magnetic field direction in the predetermined space; a second step of acquiring an error magnetic field distribution which is a difference between the measured magnetic field intensity distribution and a target magnetic field intensity distribution;

a third step of computing an arrangement condition of a shimming magnetic body forming a correction magnetic field distribution for reducing the error magnetic field distribution under a spatially and quantitatively continuous numerical value condition; a fourth step of computing an arrangement condition of a shimming magnetic body forming a correction magnetic field distribution for reducing the error magnetic field distribution under a spatially and quantitatively discrete numerical value condition; a fifth step of adding a correction magnetic field formed by the shimming magnetic body disposed on the basis of the arrangement condition acquired in the third step to the measured magnetic field intensity distribution so as to obtain a magnetic field intensity distribution after first correction; a sixth step of adding a correction magnetic field formed by the shimming magnetic body disposed on the basis of the arrangement condition acquired in the fourth step to the measured magnetic field intensity distribution so as to obtain a magnetic field intensity distribution after second correction; and a seventh step of obtaining a difference between the magnetic field intensity distribution after the first correction and the magnetic field intensity distribution after the second correction, reexamining the predetermined space or the target magnetic field intensity distribution in a case where the difference is equal to or more than a predefined predetermined threshold value so that computation is performed again from the second step, and disposing the shimming magnetic body according to the arrangement condition acquired in the fourth step in a case where the difference is less than the predefined predetermined threshold value.

Advantageous Effects of Invention

According to the present invention, it is possible to perform shimming in which homogeneity close to homogeneity obtained in ideal shimming can be acquired, on a magnet requiring an accurate magnetic field. Partial singular value decomposition is performed in advance, and computation can be performed at a high speed. As a result, it is possible to perform magnetic field adjustment work in a short period of time.

BRIEF DESCRIPTION OF DRAWINGS

FIG. 1 is a flowchart illustrating a magnet magnetic field adjustment method according to an embodiment of the present invention.

FIG. 4 is a diagram illustrating a representative shimming computation system of a horizontal magnetic field type MRI apparatus, and illustrating arrangement of shim trays (small rectangular shapes) and a magnetic field measurement plane (spherical plane).

FIG. 5 is a diagram illustrating an MRI apparatus magnet, a gradient magnetic field coil, and an imaging space.

FIG. 6 is an arrangement diagram illustrating continuously disposed shim trays for computing a virtual current potential.

FIG. 7 is a diagram illustrating a computation model in which a magnetic field of a magnetic field evaluation plane is computed on the basis of a measured magnetic field in shimming computation related to the embodiment of the present invention.

FIG. 8 is a diagram regarding eigenmode selection used to compute a virtual current potential on a current plane in computation for estimating a magnetic field at a magnetic field measurement point on the basis of a measured magnetic field.

FIGS. 10A and 10B are a diagram in which an eigenmode intensity is indicated by eigenmodes of two shim trays.

FIGS. 11A and 11B are a diagram in which an eigenmode intensity is indicated by eigenmodes of two shim trays.

FIG. 12 is a diagram illustrating an iron piece volume of a shim tray pocket and a current potential distribution of continuously disposed shim trays.

FIG. 13 is an expectation diagram illustrating a magnetic field intensity distribution after shimming on a plane of Y=0 as a distribution on a plane of an axial direction position Z and a horizontal direction position X.

FIG. 14 is a diagram illustrating a relationship between eigenmodes based on discrete arrangement and eigenmodes based on continuous arrangement.

FIG. 15 is a diagram illustrating a summary of a shimming system according to the embodiment of the present invention.

FIG. 16 is a diagram illustrating a summary of a shimming preparation computation sequence according to the embodiment of the present invention.

FIG. 17 is a diagram illustrating a summary of a shimming support computation sequence according to the embodiment of the present invention.

DESCRIPTION OF EMBODIMENTS

Embodiment

Figure 2B:
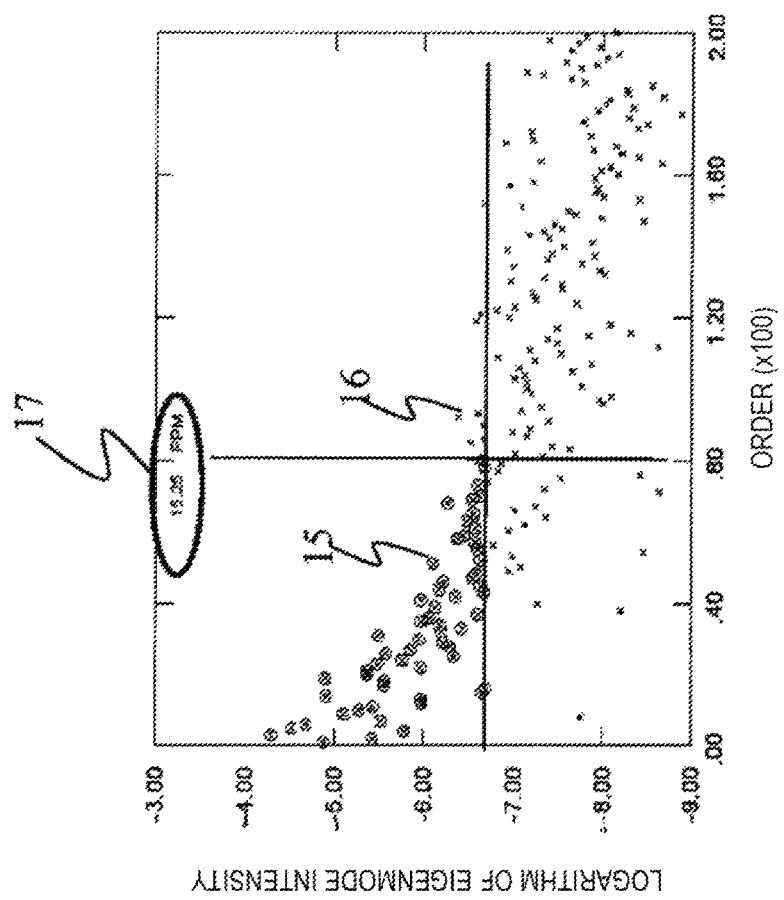
FIG. 2B illustrates an eigenmode intensity, and an eigenmode selected for shimming, in a shimming method of the related art.
Figure 2A:
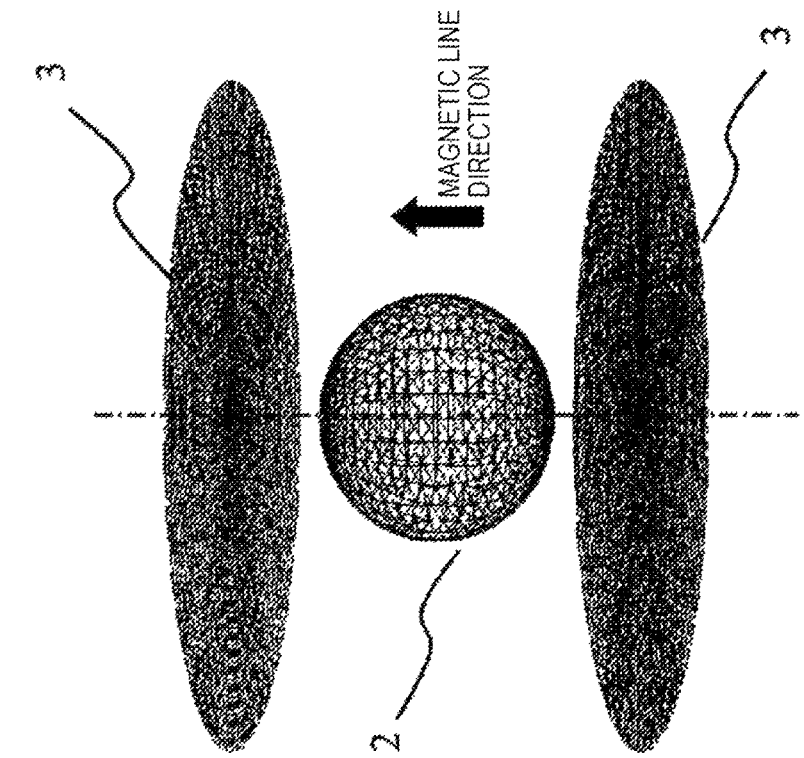
FIG. 2A illustrates a shimming computation system.

Hereinafter, as will be described in an embodiment (Example 1) of the present invention, the homogeneity of a magnetic field intensity may be defined as any one of an evaluation plane, a volume and peak-to-peak (maximum and minimum values), and a root-mean-square value), but will be described by using maximum and minimum values on a magnetic field evaluation plane and a value obtained by dividing the maximum and minimum values by an average magnetic field intensity value unless particularly mentioned. The unit thereof is ppm ($1/10^6$).

Example 1

A description will be made of the entire summary of Example 1 of the embodiment of the present invention as flows. In the present embodiment, in order to obtain a shimming magnetic body volume to be provided in discretely disposed shim trays (refer to discretely disposed shim trays 11 in FIG. 4 which will be described later), a response matrix to a magnetic field distribution is acquired through singular value decomposition on the basis of a discretized shimming iron volume (discrete shimming).

Along therewith, shimming regarding continuously disposed shim trays 14 will also be examined. Virtual shimming is performed by using virtual shim trays (refer to continuously disposed shim trays 14 in FIG. 6 which will be described later) having continuity on which a physical restriction is not imposed so that shimming results under ideal conditions are acquired, and thus reachable ideal homogeneity is recognized, and is referred to in shimming computation for the above-described discrete shim trays 11 or discrete shimming. Singular value decomposition is also applied to continuous shim trays as in PTL 1, but a direction of magnetic moment cannot be expressed as it is, and thus virtual shimming is performed assuming that magnetic moment is artificially directed in a magnetic field direction.

NPL 1 is referred to in arrangement of magnetic moment on the continuous shim trays 14. However, in this document, a current distribution is solved, and thus it is necessary to convert a current amount into magnetic moment and to set a direction thereof to a magnetic field direction artificially. Magnetic field homogeneity after shimming is disclosed in detail in NPL 2.

Here, shimming computation is defined. The shimming computation is computation in which a spatial distribution of magnetic moment to be disposed in order to correct a magnetic field distribution on a magnetic field evaluation plane to a uniform magnetic field distribution is computed, and is converted into a volume of magnetic bodies such as a volume of iron. As described above, the shimming computation includes shimming computation (discrete arrangement shimming computation) in which a spatial distribution of magnetic moment is calculated by imposing discrete arrangement conditions and shimming computation (continuous arrangement shimming computation) in which a spatial distribution of magnetic moment is calculated by imposing continuous arrangement conditions. Magnetic field evaluation before and after shimming is performed is performed on a magnetic field evaluation plane. In the shimming computation, a magnetic field distribution measured before shimming is an input, and magnetic moment obtained on the basis of the input and results of converting the magnetic moment into an arrangement position and a volume of magnetic bodies are outputs.

Next, the embodiment of the present invention will be described through explanation of the content of discrete arrangement shimming computation and continuous arrangement shimming computation, but, prior to the description, a description will be made of input information required for shimming computation, that is, magnetic field measurement means and a magnetic field measurement method on a magnetic field evaluation plane.

Figure 3A:
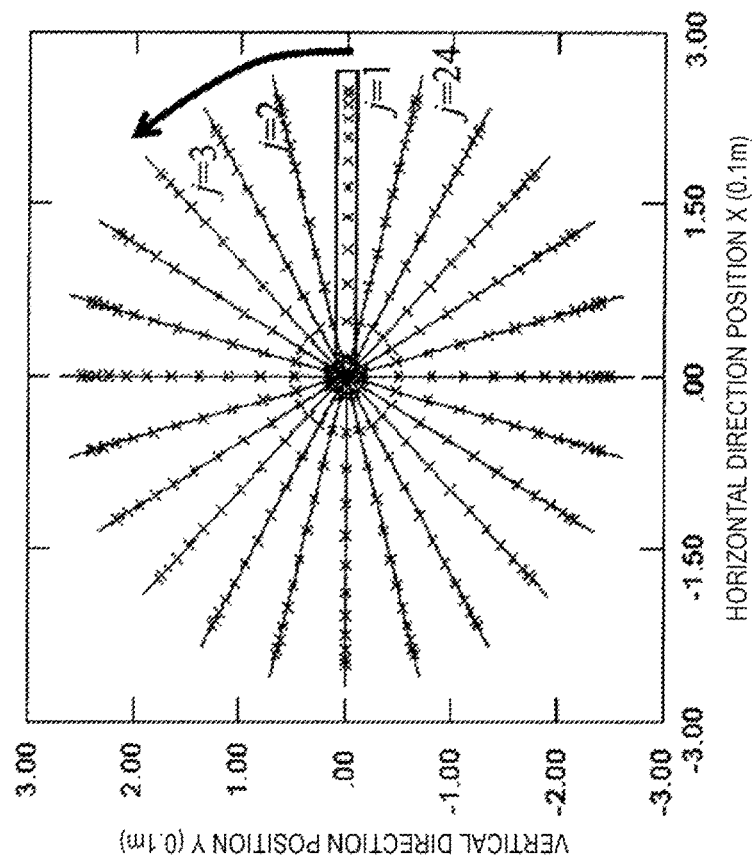
FIGS. 3A and 3B are a diagram illustrating a magnetic sensor and a magnetic field measurement tool, respectively.
Figure 3B:
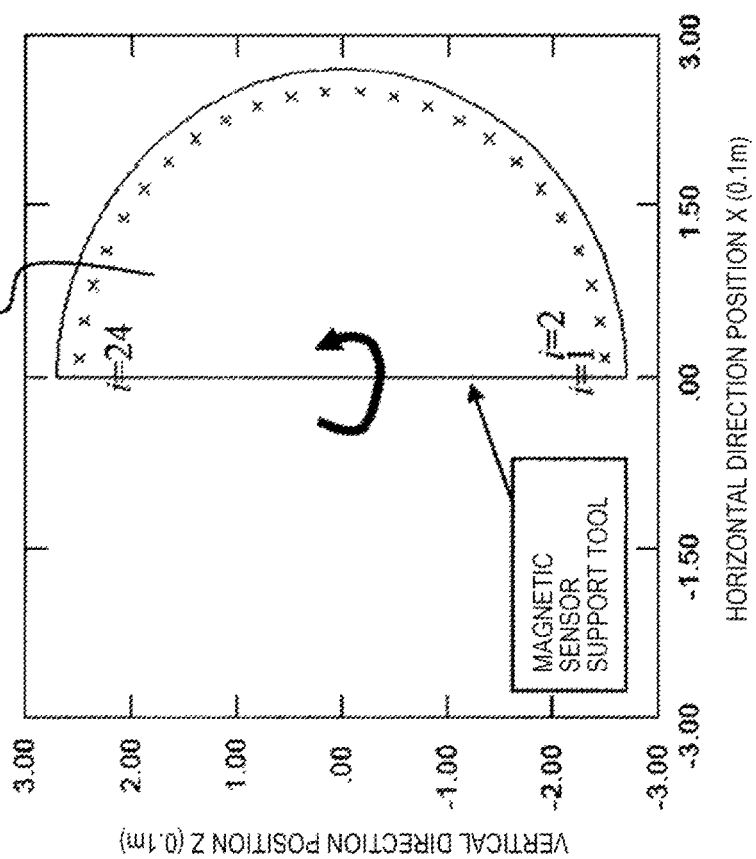

FIGS. 3A and 3B are a diagram illustrating a magnetic sensor and a magnetic field measurement tool. In other words, FIG. 3A illustrates a summary of the magnetic field measurement tool, and illustrates a support plate 20 and installation positions (x marks) of magnetic sensors. FIG. 3B illustrates a state in which the magnetic field measurement tool is rotated centering on a predetermined axis, and a magnetic field is measured at a plurality of positions. In this example, measurement is performed at twenty-four angles, that is, a pitch of 15 degrees. In actual shimming, for example, a plurality of bar-shaped discretely disposed shim trays 11 disposed as illustrated in FIG. 4, shim pocket 5 groups disposed in the discretely disposed shim trays 11, and a magnetic field measurement tool as illustrated in FIGS. 3A and 3B are used. The magnetic field measurement tool illustrated in FIG. 4 is an example, has an axis which is parallel to a magnetic field in a horizontal direction, and performs measurement which is rotationally symmetrical to the axis, but, of course, a spherical support plate may be prepared, and magnetic sensors may be disposed on a surface thereof.

Typically, the shim pockets 5 are disposed inside a cylindrical gradient magnetic field coil 24 (refer to FIG. 5), and the shim pocket 5 groups are also disposed in a cylindrical shape. The shim pockets 5 (that is, shimming magnetic bodies) are disposed to surround a magnetic field measurement plane 8, and magnetic field measurement points (positions where magnetic sensors are to be disposed) are set on the magnetic field measurement plane 8.

In the magnetic field measurement tool illustrated in FIG. 3A, twenty-four (i=1 to 24) magnetic sensors are disposed on the support plate 20 so as to form a single measurement plane, and, magnetic field measurement is performed at twenty-four angles (j=1 to 24) by rotating this magnetic field measurement plane centering on a z direction in a circumferential rotation direction as illustrated in FIG. 3B.

As a result, magnetic field measurement can be performed at 576 points on the magnetic field measurement plane 8 (in this case, a spherical plane). The magnetic field measurement points are provided on the spherical plane, and all of the magnetic field measurement points can be positionally moved in the same amount and direction by changing a fixed position of the magnetic field measurement tool. An amount and a direction of the movement will be hereinafter referred to as movement of the center of the magnetic field measurement point group. A position as the central position of magnetic field measurement is an axial direction central position on a rotation axis of the half-moon-shaped magnetic sensor support plate 20 at the origin position in FIG. 3A. The position is a geometrical average value of magnetic field measurement positions.

The above description relates to an example of magnetic field measurement performed in shimming of the present embodiment. If the magnetic field measurement is completed, shimming computation is performed on the basis of acquired information regarding a magnetic field.

First, continuous arrangement shimming computation will be described. In the continuous arrangement shimming computation, continuously disposed shim trays (which are not real objects) are set, and virtual shimming computation is performed. In this computation, a cylindrical plane 14 as illustrated in FIG. 6 is assumed, and a magnetic moment distribution on the cylindrical plane 14 is calculated. FIG. 6 is a diagram illustrating arrangement of continuously disposed shim trays for computing a virtual current potential. It is assumed that the virtual continuously disposed shim trays 14 form the cylindrical plane with an aggregate of triangular elements. A virtual current potential (hCP) is defined in each vertex (node) of the triangular element. If the hCP is integrated in terms of area on the continuously disposed shim trays 14, magnetic moment of the integral region can be calculated.

The term "continuous" mentioned here indicates continuity compared with the term "discrete" which will be described later with respect to a volume of shimming magnetic bodies to be disposed or arrangement positions of shimming magnetic bodies. The term "continuous" in the present example does not necessarily indicate strict continuity on mathematics, but may indicate that there is a degree of freedom in a value which can be taken with respect to an arrangement volume or an installation position compared with a case of the term "discrete" described in the present example, that is, dense arrangement is permitted in terms of space, and values other than standardized numerical values are used in terms of arrangement volume.

Next, discrete arrangement shimming computation will be described. FIG. 4 is a diagram illustrating a representative shimming computation system of a horizontal magnetic field type MRI apparatus, and is a diagram illustrating arrangement of shim trays (small rectangular shapes) and a magnetic field measurement plane (spherical plane). In the discrete arrangement shimming computation, a volume of magnetic bodies disposed in the shim pockets 5 of the discretely disposed shim trays 11 illustrated in FIG. 4 is calculated. Magnetic bodies provided in the shim pocket 5 are magnetized by a static magnetic field, magnetic moment generates a magnetic field due to the magnetization, and thus a magnetic field distribution in the magnetic field evaluation plane 2 is corrected (subjected to shimming). A magnetic field generated by magnetic moment is computed in order to achieve this purpose.

Generally, magnetic moment m in point arrangement may be defined as a magnetic dipole of m=(mX,mY,mZ) [unit: $Am^2$] in any direction. Generally, a magnetic field B formed by the magnetic moment m at a separated position of a position vector r=(X,Y,Z) may be expressed by the following equation.

$$B=(10^{-7})\{3(m\cdot r)r/r^2-m\}/r^3 \quad (1)$$

A BZ component of an axial direction magnetic field treated in shimming is expressed by the following equation.

$$BZ=10^{-7}\{-mZ/R^3+3mXXZ/R5+3mYYZ/R5+3mZZ^2/R5\} \quad (2)$$

Iron pieces disposed through shimming are mainly magnetized in an axial direction, and a magnetic dipole caused by the magnetization has three-dimensional directions. However, since a magnetic field which magnetizes the iron pieces is mainly directed in the axial direction, even if only mZ is normally treated, an error occurring due to this is slight. Magnetic moment of saturated pure iron (2.15 T) per unit volume is $1.711\times10^6$ $Am^2/m^3$ Except for the pure iron, this value becomes small, for example, in a silicon steel sheet. Since magnetic moment depends on a material and a peripheral magnetic field environment, a magnetic dipole intensity per unit volume is required to be measured when applied to an actual apparatus.

When organized by adding the number j to the shim pockets 5 in FIG. 4 by using Equation (1) or (2), a magnetic field at an i-th magnetic field measurement position (magnetic field evaluation plane 2) has a linear relational expression with respect to an iron volume $V_j$ ($m^3$) of each pocket as follows.

$$BZ_i=\Sigma AZ_{ij}V_j \quad (3)$$

If this is organized, $V^{SM}$ is computed for a magnetic field intensity $B^{TG}$ which is desired to be generated through shimming, and a volume thereof is disposed in the shim pocket 5.

$$B^{TG}\cong AV^{SM} \quad (4)$$

Here, both sides in Expression (4) are approximately close values, and are not exactly the same as each other generally. Thus, ≅ written. The matrix A is irregular, and is a so-called ill-posed problem.

On the other hand, in a case of the continuously disposed shim trays 14 illustrated in FIG. 6, a virtual current potential is present in a contact point between triangular elements, and has magnetic moment. A current potential Tk of a contact point k may be understood as the current Tk being circumferentially rotated in peripheral elements of the contact point. Thus, a normal current potential has magnetic moment expressed by Equation (5).

$$M_i=\Sigma T_i Sk/3 \quad (5)$$

Here, $M_i$ indicates magnetic moment ($Am^2$) of an i-th contact point, and Sk indicates an area [$m^2$] of an element k having the i-th contact point as a vertex. Summation is performed on the element k related to the contact point i. A general current potential has magnetic moment in a direction which is perpendicular to an element surface, but, herein, a description is made by using a virtual current potential. For the virtual current potential hCP, all pieces of magnetic moment are made to be directed in a magnetic field direction, that is, treated as Z direction components. Since a magnetic field is generated by magnetic moment as in a magnetic piece, a magnetic field generated by hCP is organized as in Expression (4), and the following Expression is obtained.

$$B^{TG}\cong AT^{SM} \quad (6)$$

Here, $T^{SM}$ is a vector having an hCP value of each contact point in a vector element. A is a magnetic field response matrix to a magnetic field measurement position from a virtual current potential. The matrix is a matrix having a value and a size which are different from those in Expression (4), but both of the matrices are response matrices, and thus are indicated by A for simplification.

As described above, an equation to be solved is a linear equation system in both of shim tray models (5 and 14). In Expressions (4) and (6), an input is an iron volume or an hCP value, and an output is a magnetic field distribution, but, herein, conversely, a problem of obtaining $V^{SM}$ or $T^{SM}$ causing $B^{TG}$ to be generated, a so-called inverse problem is solved.

For simplification of a solution description, $V^{SM}$ and $T^{SM}$ are written as $I^{SM}$, and a solution of the following expression.

$$B^{TG}\cong AI^{SM} \quad (6)$$

Here, $B^{TG}$ indicates a magnetic field intensity distribution at a magnetic field intensity measurement point before shimming, and is expressed by the following equation.

$$B^{TG}=B^0-B^{MG} \quad (7)$$

Here, $B^0$ is a vector of a uniform magnetic field distribution (a magnetic field distribution of a static magnetic field in a case of an MRI apparatus), and has the same value such as 1.5T in elements thereof. $B^{MG}$ is a vector indicating a magnetic field distribution at a magnetic field evaluation point before shimming.

In a description of a solution of $B^{TG}$, the superscripts of $B^{TG}$ and $I^{SM}$ will be omitted.

An operation amount is indicated by I, and this indicates a volume of iron pieces to be disposed, or a current potential. If A is regular, an inverse matrix is $A^{-1}$. However, herein, the matrix A is not regular, and thus there is no inverse matrix. Thus, A is solved by using a regularization method using truncated singular value decomposition. In order to enable a discussion about improvement of performance of shimming (more improved homogeneity is obtained with a smaller magnetic body volume), weight matrices $W_B$ and $W_I$ are introduced. The matrices are respectively square diagonal matrices having the same order as magnetic field data and the number of current values, and diagonal components thereof are inverse numbers of weights. The former matrix is expressed as follows.

$$W_B B = W_B A W_I^{-1} W_I I \quad (7)$$

In the following description, a magnetic field $B^{REC}$ for approximately reconstructing a target magnetic field B to be generated through shimming is obtained. In this equation, A' is assumed to be $W_B A W_I^{-1}$. If singular value decomposition (SVD) is applied, the following equation is obtained.

$$A' = \Sigma u_i \lambda_i v_i^t \quad (8)$$

Here, $v_i$ is a matrix indicating an eigen distribution of a current distribution, $u_i$ is a matrix indicating an eigen distribution of a magnetic field distribution, and $\lambda_i$ is a singular value indicating conversion thereof. This combination of $v_i$, $u_i$, and $\lambda_i$ is referred to as an eigenmode. Intuitively, $v_i$ indicates a magnetic body volume to be disposed or magnetic moment, $u_i$ indicates an eigen magnetic field distribution corresponding to $v_i$, and $\lambda_i$ indicates how $u_i$ is output with respect to $v_i$, that is, an amplification ratio of $v_i$ to $u_i$.

Therefore, as $\lambda_i$ increases, an intensity distribution of a formed magnetic field becomes larger with respect to a small volume of disposed magnetic bodies becomes larger, and, conversely, as $\lambda_i$ decreases, the sensitivity of an intensity of a generated magnetic field is lowered with respect to a volume of disposed magnetic bodies. It can be seen from this that efficient (the homogeneity of a magnetic field intensity is achieved with a small arrangement volume of shimming magnetic bodies) magnetic field adjustment is preferably performed focusing on an eigenmode in which $\lambda_i$ is large.

Eigenmode numbers which will be described later are allocated to eigenvalues in descending order.

If Equation (8) is assigned to Equation (7), a current distribution for reconstructing $B^{TG}$ may be approximately computed according to the following equation.

$$W_I I = A^* B^{TG} \quad (9)$$

$W_B$ is a shimming point and is thus not given a difference in accuracy, and a unit matrix is omitted. Here, $A^*$ is expressed as follows, and is a general inverse matrix of computed A.

$$A^* = \rho v_i u_i^t / \lambda_i \quad (10)$$

Summation is performed by selecting an eigenmode which is required to maintain magnetic field accuracy. Here, Equation (9) is rewritten as follows.

$$I = \Sigma n_p^{1/2} P_i^{TG} W_I^{-1} v_i / \lambda_i [A, m^3, \text{ or } Am^2] \quad (11)$$

Here, $P_i^{TG}$ is as follows. $P_i^{TG} = u_i^t B^{TG} / n_p^{1/2} [T] \quad (12)$ $P_i^{TG}$ is an eigenmode intensity which is required to reconstruct $B^{TG}$. As can be seen from $u_i^t B^{TG}$, the eigenmode intensity can be recognized as an inner product value between an eigen magnetic field distribution in an i-th eigenmode and a target magnetic field. Therefore, it can be said that $P_i^{TG}$ indicates reproducibility using the eigen magnetic field distribution in the i-th eigenmode for the target magnetic field.

In addition, $n_p$ indicates the number of magnetic field evaluation points. As an eigenmode intensity, an intensity obtained by dividing a predetermined intensity by $n_p^{1/2}$ is used. This is because the magnetic field intensity in the above equation is substantially a value close to an average value of respective magnetic field evaluation values.

Generally, the reconstruction magnetic field distribution $B^{REC}$ at a magnetic field evaluation position is expressed by addition of eigenmodes by using the intensity $P_i^{TG}$, and is thus added to a measured magnetic field $B^{MG}$ as follows.

$$B^{REC} = \Sigma n_p^{1/2} P_i^{TG} u_i + B^{MG} \quad (13)$$

A magnetic field distribution after shimming work may be estimated as $B^{REC}$.

Here, summation in Equation (13) is performed from a first eigenmode to an $M_D$-th eigenmode corresponding to a necessary number. The shimming work indicates the whole repetitive work in which magnetic body arrangement is performed through shimming support computation, and magnetic field measurement is performed after the arrangement. The shimming support computation is the concept including shimming computation, and includes magnetic field estimation computation at a magnetic field evaluation point based on a measured magnetic field, and the current homogeneity evaluation and validity evaluation of shimming computation, in addition to the shimming computation. A difference between a target magnetic field and a reconstructed magnetic field is a residual magnetic field, and a residual magnetic field $B^{res}$ at a magnetic field evaluation position is as follows.

$$B^{res} = B^0 - B^{REC} \quad (14)$$

Generally, if the eigenmode number $M_D$ which is an upper limit of an eigenmode, added in Equation (13) is increased, a residual magnetic field is reduced. However, the eigenmode number $M_D$ is preferably increased in order to obtain an extremely small residual magnetic field, but is determined in relation to arrangement and a volume {Equation (11)} of shimming magnetic bodies which can be actually disposed.

If the solution described here is used, accuracy can be adjusted with the eigenmode number $M_D$, and shimming can be performed with appropriate magnetic body arrangement. Since the above-described computation can be performed by using both of the systems of the continuously disposed shim trays 14 and the discretely disposed shim trays 11, better shimming conditions can be set through comparison between ideal shimming based on continuous arrangement shimming computation 32 and discrete arrangement shimming computation 31.

A virtual current potential (hCP) is also computed in the same manner as a typical current potential (refer to NPL 2). Magnetic moment can be converted into a current in the same method as in NPL 2 except that a direction of the magnetic moment corresponding to hCP is a magnetic field direction. Therefore, a current can be obtained on the basis of hCP, and a magnetic field can be computed according to the Biot-Savart law. A magnetic field can also be computed by using Equation (1) on the basis of magnetic moment of hCP.

In other words, by using the solution for the discretely disposed shim trays 11, it is possible to accurately compute an arrangement amount of shimming magnetic bodies in each shim tray, and also to perform comparison with reachable homogeneity in a case where ideal shimming can be performed with the continuously disposed shim trays 14. Thus, it is possible to prevent deterioration in homogeneity evaluation after shimming due to discretized arrangement of the shim trays. It is also possible to design arrangement of the discretely disposed shim trays 5 for preventing deterioration in homogeneity evaluation after shimming due to discretized arrangement of the shim trays.

Hereinafter, a shimming method of the present embodiment will be described in more detail.

FIG. 1 illustrates a summary of a shimming method of the present embodiment. FIG. 1 is a flowchart illustrating a magnet magnetic field adjustment method according to the embodiment of the present invention. In this shimming method, if work is started, a process of reading (S01) of a preparation computation result is performed as necessary. After, this process is performed, a process of magnetic field intensity distribution measurement (S02) is performed, and then the flow proceeds to homogeneity evaluation (S03). If homogeneity satisfies a specification in the homogeneity evaluation (S03), the shimming is finished. If homogeneity does not satisfy the specification in the homogeneity evaluation (S03), shimming support computation (S04) is performed. Shimming work (S05), for example, iron piece arrangement or current amount adjustment for a shim coil is performed on the basis of the obtained result. After the shimming work (S05) is completed, the flow returns to the next homogeneity evaluation (S02), and a series of work is performed. The processes from S02 to S5 are performed until homogeneity satisfies the specification.

FIG. 15 illustrates a summary of a shimming system for performing the shimming method. A functional configuration diagram in FIG. 15 is an example for simplification of description, and may be further subdivided, and the shimming system may be configured through a combination with a plurality of computers or servers. It is assumed that various measurement results or calculation data is preserved in a specimen transfer device included in a general computer, an externally connected database, or the like, and is read to a processing device, and computation is performed.

As illustrated in FIG. 15, the shimming system of the present example is roughly divided into and formed of a shimming preparation computation section 101 and a shimming support computation section 100. The shimming preparation computation section 101 mainly includes a preparation computation unit and a storage unit. Functions of each unit will be described later.

The shimming support computation section 100 mainly includes a magnetic field interpolation/extrapolation computation unit 102, a homogeneity evaluation unit 103, a discrete arrangement shimming computation unit 104, a continuous arrangement shimming computation 105, a shimming computation evaluation unit 106, and a display unit 107. The arrows in the figure indicate input and output directions for each functional block.

Magnetic field measurement and shimming work illustrated outside the chain line are the work content performed by a worker, and thus are not included in the configuration of the shimming system, but indicate a flow of outputting an instruction to the worker, a flow of a magnetic field measurement result being input by the worker, and the like.

The shimming work indicates computation work, iron piece arrangement work, and magnetic field measurement work in the shimming support computation section 100, and the work is repeatedly performed several times until sufficient homogeneity is obtained. The work being repeatedly performed several times mainly copes with an error of a magnetic body volume occurring during magnetic body arrangement.

Next, a description will be made of each of the shimming preparation computation section 101, the shimming support computation section 100, and magnetic field measurement and iron piece arrangement work. Computation or work performed in each portion will be described by using a reference sign in which the sign S indicating a step is combined with a number.

First, the shimming preparation computation section 101 performs a series of computation processes recommended to be performed before starting the shimming work. Results of the computation processes performed here may be preserved in advance in a database of a computer or the like which is used for shimming.

FIG. 16 is a diagram illustrating a summary of a shimming preparation computation sequence regarding the embodiment of the present invention. The work to be performed in the shimming preparation computation section 101 includes, as illustrated in FIG. 16, "selection (S001) of a magnetic field evaluation position", "selection (S002) of a shape of continuously disposed shim trays", "selection (S003) of a shape of discretely disposed shim trays", "selection (S004) of a spherical current plane shape", "singular value decomposition (S005) regarding continuously disposed shim trays", and "singular value decomposition (S006) regarding a spherical current plane shape".

In the "selection (S101) of a magnetic field evaluation position", a plane for evaluation (homogenization) in shimming separately from a magnetic field measurement position. Typically, a spherical plane or a spheroidal plane is set in the same manner as in a magnetic field measurement plane, and a magnetic field evaluation points (hundreds to thousands) of the same extent as the number of magnetic field evaluation points provided on the magnetic field measurement plane are disposed on the plane. As will be described later, according to the shimming method of the present embodiment, any "magnetic field evaluation position" may be set through "magnetic field interpolation/extrapolation computation". Since the magnetic field evaluation point (plane) may be changed in the shimming work repeatedly performed several times, and thus a plurality of combinations of magnetic field evaluation points (planes) are prepared. In other words, a magnetic field evaluation point 2 is to be prepared not in a single plane but in a plurality of planes.

In the "selection (S002) of a shape of continuously disposed shim trays", for example, as illustrated in FIG. 5, a case where the discretely disposed shim trays 14 are disposed in the gradient magnetic field coil 24 inside a magnet 10 is assumed, and a shape of the continuously disposed shim trays 14 is determined as a cylindrical plane in which a shape (a radius value and a length) of the gradient magnetic field coil 24 is reflected. FIG. 5 is a diagram illustrating an MRI apparatus magnet, a gradient magnetic field coil, and an imaging space. In this method, even if a sectional shape of the gradient magnetic field coil 23 is not a cylindrical shape, but is an elliptical shape or any other shapes, the continuously disposed shim trays 14 may be disposed along the section. In the "singular value decomposition (S005) regarding continuously disposed shim trays", according to the present embodiment, an eigenmode is computed in advance through singular value decomposition on the continuously disposed shim trays 14, and the eigenmode is preserved in a database B along with the shape of the continuously disposed shim trays determined in S002 and information regarding the magnetic field evaluation positions determined in S001.

In other words, in a magnet apparatus in which a magnetic field evaluation plane (a plurality of planes may be provided) is clearly expected to an extent, and a shimming system is already defined, an eigenmode in the same system is acquired before shimming work is performed, and thus it is possible to efficiently perform shimming work for each apparatus in a case where a plurality of magnet apparatuses of the same system are present. This is because the number of nodes of triangular elements forming the continuously disposed shim trays 14 is thousands, and is about one digit larger than the number of discretely disposed shim trays. Thus, the time required to obtain the eigenmode ($v_i$, $u_i$, $\lambda_i$) through singular value decomposition on the response matrix in Expression (6) as in Equation (8) is longer than in singular value decomposition on the response matrix in Expression (4). If this processing time can be permitted, the computation may be performed during actual shimming work.

On the other hand, the response matrix in Expression (4) regarding the discretely disposed shim trays 5 is computed during shimming computation which is performed along with the shimming work. This is because the number of shim pockets 5 is relatively small, singular value decomposition on the response matrix can be performed in a short period of time, and a weight of each shim pocket 5 may be changed (in a case where the weight of the shim pocket 5 is not changed, the weight may be computed in advance).

The "selection (S003) of a shape of discretely disposed shim trays" indicates that a shape, the number, and positions of shim tray pockets 5 to be actually used are reflected and prepared.

The "selection (S004) of a spherical current plane shape" indicates work of determining a spherical current plane shape used for computation for estimating magnetic field data or the like on the magnetic field evaluation plane on the basis of magnetic field data measured in advance on the magnetic field measurement plane 8. Also in this case, since an eigenmode is computed through singular value decomposition so that hCP values at thousands of nodes are determined in the same computation method as in the continuously disposed shim trays 14, computation time increases. Thus, if computation of singular value decomposition is performed in a preparation stage, it is possible to improve efficiency of work in a case where shimming is performed on a plurality of magnet apparatuses of the same system (singular value decomposition (S006) regarding a spherical current plane shape).

FIG. 7 illustrates a computation model of an eigenmode in a "spherical current plane shape". In other words, FIG. 7 is a diagram illustrating a computation model in which a magnetic field of a magnetic field evaluation plane is computed on the basis of a measured magnetic field in shimming computation according to the embodiment of the present invention. The computation model is expressed by, for example, two spherical planes, and includes the magnetic field measurement plane 8 inside thereof, and a current plane 1 in which a current distribution causing a magnetic field intensity distribution in the magnetic field measurement plane 8 on computation to be reproduced is assumed outside thereof.

The current plane 1 is a closed curved plane. Even in a case where there is an opening, the opening is a curved plane, a size thereof is about 1/10 or less of $4\lambda$ as a solid angle from the apparatus center, and the opening surrounds the magnetic field measurement plane 8 as a whole. The computation content is the same as in Equation (1) to Equation (10), singular value decomposition is performed, and eigenmode data is preserved in a database A along with magnetic field measurement point positions or magnetic field evaluation point positions.

The above-described preparation is performed, and then shimming work is started. The work is repeatedly performed, and is finished at the time at which sufficient homogeneity for a specification can be obtained. The repeatedly performed work is mainly classified into (a) manual work (iron piece arrangement (S05), and magnetic field measurement work (S02)) and (b) shimming support computation S04 performed by a computer. The following description focuses on the shimming support computation S04, but relates to preparation for this. The work is repeatedly performed in the order of the magnetic field measurement S02, the shimming support computation S04, and the iron piece arrangement S05, and is performed until a sufficiently uniform magnetic field can be obtained.

Hereinafter, a description will be made of magnetic field measurement/iron piece arrangement work 35.

The "magnetic field measurement (S01)" is performed by disposing magnetic sensors indicated by x in FIG. 3A. In FIG. 3A, the magnetic sensor support plate 20 is a part of a support tool (not illustrated) having a central axis as a rotation axis, but magnetic sensors (indicated by x in the figure) are fixed to the plate. In FIG. 3A, twenty-four (i=1 to 24) magnetic sensors are disposed, and magnetic field measurement is performed on twenty-four magnetic field measurement planes (j=1 to 24) in the circumferential rotation direction. As a result, magnetic field measurement at 576 points on the magnetic field measurement plane (in this case, a spherical plane) can be performed. Such magnetic field measurement values are used for computation of a virtual current distribution on the above-described spherical current plane.

Hereinafter, a description will be made of a process in the shimming support computation section 100.

FIG. 17 is a diagram illustrating a summary of a shimming support computation sequence according to the embodiment of the present invention. A computation process performed by the shimming support computation section 100 may include, as illustrated in FIG. 17, "magnetic field interpolation/extrapolation computation (S201)", "homogeneity evaluation (S202)", "discrete arrangement shimming computation (S203)", "continuous arrangement shimming computation 32 (S204)", and "shimming content evaluation (S205)".

In the "magnetic field interpolation/extrapolation computation (S201)", magnetic fields at the magnetic field evaluation point positions are computed and evaluated on the basis of the magnetic field data of the measured magnetic field acquired in step S101. The data regarding the eigenmodes acquired through singular value decomposition on the computation model in FIG. 7 is read from the database A and is used. Weights at contact points on the spherical virtual current plane 1 are assumed to be all the same as 1.0. FIG. 8 illustrates a result of plotting the eigenmode intensities obtained according to Equation (12) with a function of numbers arranged in the order of the magnitude of a singular value with respect to the eigenmodes read from the database A. FIG. 8 is a diagram related to eigenmode selection used to compute a virtual current potential on a current plane in computation for estimating a magnetic field at a magnetic field evaluation point on the basis of a measured magnetic field. In this figure, a magnetic field measurement position is used as a magnetic field evaluation point.

Specifically, the eigenmode intensity illustrated in FIG. 8 is displayed logarithmically. A bent line indicates an error between a computation result when a magnetic field is computed at a measured magnetic field position on the basis of an eigenmode, and a measured magnetic field, $B^{res}$ is computed with a function of the eigenmode number $M_D$ which is an upper limit of the eigenmode added when computation is performed according to Equation (13), and a peak-to-peak value of a value of each element is displayed. In other words, this shows that an error of a magnetic field distribution reconstructed by using a current on the spherical current plane is $\pm 0.1$ μT if the eigenmode number $M_D$ is 550, and a magnetic field can be estimated and computed within such a computation error. It is preferable that the eigenmode number $M_D$ and the number of eigenmodes to be selected are large. Therefore, a value close to the number of computable eigenmodes is preferably set, and, in a case where the number of measurement points is larger, a greater eigenmode number $M_D$ can be selected. If an eigenmode to be selected is defined, a current distribution on the current plane 1 is computed this time by using Equations (11) and (12). Since a magnetic field which is computed by using a current on the virtual current plane 1 can be computed at any point if a region is surrounded by the current plane, a magnetic field evaluation point during shimming is defined separately from a magnetic field measurement point, and a magnetic field may be computed and may be used as an input in the subsequent shimming computation.

In other words, the shimming system of the present embodiment includes the "magnetic field interpolation/extrapolation computation" unit, and can thus estimate, on the basis of a measured magnetic field acquired at a certain single magnetic field measurement point, a magnetic field at a point which is different from the magnetic field measurement point with high accuracy. This shows that, for example, even if the measurement is performed on a magnetic field measurement plane corresponding to a spherical plane of 40 cm, a magnetic field intensity distribution on a spherical plane of 30 cm or any spherical plane smaller than that can be estimated in microtesla order or less. Taking into consideration the fact that actual measurement is necessary in a case where magnetic field homogeneity is evaluated on locations other than a magnetic field measurement plane in a shimming method of the related art, a burden on a worker is considerably reduced since actual measurement can be omitted.

Since a magnetic field at any magnetic field evaluation point can be estimated through the "magnetic field interpolation/extrapolation computation", a volume root-mean-square value in the "homogeneity evaluation (S202)" which will be described later can be obtained with high accuracy.

In the above-described "magnetic field interpolation/extrapolation computation", there may be a case where there is no eigenmode selection condition causing magnetic field evaluation accuracy to be high. For example, this case is a case where a current plane is separated from a magnetic field measurement position. This is not problematic in principle, but there is a limit in computation accuracy in terms of the number of bits during computation in an actual computer, and thus a computational problem may occur due to the influence. In a case where an error of a magnetic field distribution is understood from a computation result, and sufficient accuracy cannot be obtained, a reexamination is performed by changing a position and a shape of a current plane.

The "homogeneity evaluation (S202)" indicates a process of evaluating homogeneity the magnetic field measured in S101 and the magnetic field estimated through the "magnetic field interpolation/extrapolation computation", and determining validity thereof. If favorable homogeneity is obtained (specification is satisfied), the shimming work is finished. If the homogeneity is lower than the specification, the shimming work is repeatedly performed, and, specifically, the following discrete arrangement shimming computation S203 or continuous arrangement shimming computation S204 is performed.

Whether or not homogeneity is high is evaluated by using a peak-to-peak (PP) value on a magnetic field evaluation plane 2 (a spherical plane or an elliptical surface) of a specification, or a volume root-mean-square volume value computed inside thereof. For example, there is a specification in which magnetic field amplitude within a PP value of 3 ppm in a sphere with 40 cmϕ is permitted. The magnetic field in the specification is applied to a value of a magnetic field distribution computed on the basis of not only a measured magnetic field but also a current on the spherical current plane 1 illustrated in FIG. 7.

Next, a description will be made of "discrete arrangement shimming computation 32 (S203)". The computation performed here includes "shim tray weight setting (S301)", "discretely disposed shim tray singular value decomposition (S302)", "target magnetic field/eigenmode selection condition determination (S303)", and "eigenmode intensity computation/eigenmode selection/shimming magnetic body volume computation/magnetic field prediction after execution of shimming (S304)".

The "shim tray weight setting (S301)" indicates that $W_I$ in Equation (7) is input with respect to the discretely disposed shim trays 11. A weight $d_{ii}$ is a diagonal element component of $W_I$, and is located as $1/d_{ii}$. If $d_{ii}$ is increased, a shimming iron volume is preferentially allocated. For example, the weight is used to correct a distance between a magnetic field evaluation plane and a shim tray, or is used in a case where shimming iron pieces are not desired to be disposed at a distant position. As shown in Equations (1) and (2), a magnetic field generated by magnetic moment is weakened in proportion to the cube of a distance, and thus a large volume of iron is required to be disposed at a position of the distant shim pocket 5. Thus, it is possible to improve computation accuracy through weighting.

In the "discrete arrangement shimming tray singular value decomposition (S203)", a response matrix for a magnetic field on the magnetic field evaluation plane 8 is obtained on the basis of a shimming iron volume (magnetic body volume) disposed in the shim pockets 5, the response matrix is subject to singular value decomposition, and a shimming iron volume, and an eigen distribution and a singular value of the magnetic field are obtained. The response matrix here is, for example, a response matrix to 576 magnetic field evaluation points as in the previous example from thousands to hundreds of shim pockets 5. Magnetic field evaluation points in shimming computation for the discretely disposed shim trays 11 are made the same as the magnetic field evaluation points in shimming computation for the continuously disposed shim trays 14 by using the values which are determined in advance in the "selection (S001) of a magnetic field evaluation position" in FIG. 16.

Of the "target magnetic field setting and eigenmode selection condition determination", in the target magnetic field setting, a value of a target magnetic field $B^0_i$ which is a target intensity of a uniform magnetic field is determined on the basis of a measured magnetic field value and a magnetic field intensity at the magnetic field evaluation point computed and estimated through the "magnetic field interpolation/extrapolation computation" after magnetic field adjustment is performed. Here, the subscript i of $B^0_i$ indicates a magnetic field intensity at an i-th magnetic field evaluation point. $B^0_i$ is an element of $B^0$ in Equation (14). Herein, since magnetic field evaluation during shimming is performed, a magnetic field evaluation point which is different from a magnetic field evaluation point on the magnetic field measurement plane 8 is used. In other words, a magnetic field evaluation point is set in relation to a region which is considered to be important in terms of imaging.

Figure 9B:
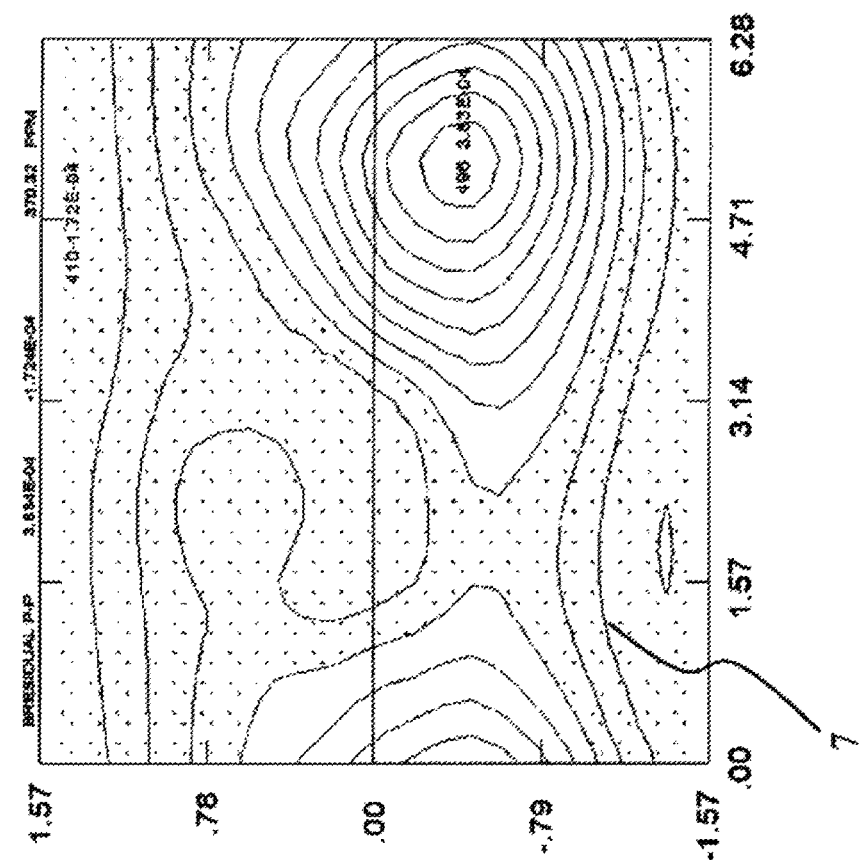
FIG. 9B illustrates a contour line of a magnetic field distribution obtained through computation using a magnetic field evaluation plane.
Figure 9A:
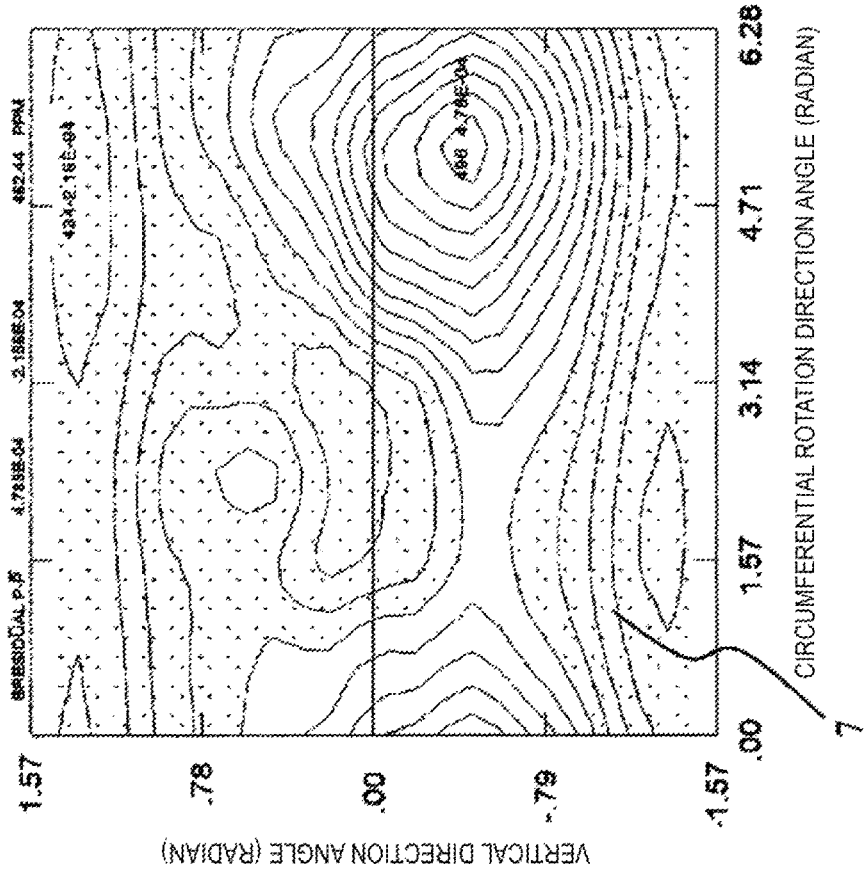
FIG. 9A illustrates a contour line of a magnetic field distribution obtained through computation using a measured magnetic field.

FIG. 9A illustrates a measured magnetic field and FIG. 9B illustrates a magnetic field distribution at magnetic field evaluation points. In other words, FIG. 9A is a contour line diagram of a magnetic field distribution computed on the basis of the measured magnetic field, and FIG. 9B is a contour line diagram of a magnetic field distribution on the basis of the magnetic field evaluation plane. The upper parts illustrate the maximum and minimum values of error magnetic fields and homogeneity obtained in terms of pp values. The measured magnetic fields here are measured at 576 magnetic field measurement points on a spherical plane with a diameter of 50 cm by using the magnetic field measurement tool in FIGS. 3A and 3B. On the other hand, the graph illustrated in FIG. 9B magnetic field evaluation points of the same number are defined on a spherical plane with a diameter of 45 cm, and a magnetic field distribution is reconstructed. A magnetic field variation (maximum-minimum-value width) is small on the magnetic field evaluation plane 2 which is a smaller spherical plane, but distribution shapes are approximately similar to each other. The shimming support computation section 34 performs shimming support computation of obtaining magnetic moment arrangement (continuously disposed shim trays 14) and iron arrangement (discretely disposed shim trays 11) so that a magnetic field on the magnetic field evaluation plane 2 which is a set of magnetic field evaluation points is evaluated and is made uniform.

The eigenmode selection condition determination indicates that an eigenmode to be added in Equations (11) and (13) is selected. The eigenmode intensity obtained according to Equation (12) is referred to, and an eigenmode is selected so that $B^{res}$ obtained according to Equation (14) is made sufficiently smaller than in the specification. However, an eigenmode is not clearly defined at the time of starting the discrete arrangement shimming computation 31. Thus, as will be described later, shimming is performed virtually through computation in order to proceed to shimming work, and conditions for obtaining sufficient homogeneity with respect to the specification in a magnetic moment amount (iron piece volume) which can be disposed are selected.

Also in the continuous arrangement shimming computation (S204), the "target magnetic field setting and eigenmode selection condition determination" are performed. However, it is noted that an eigenmode here is different from that in the discrete arrangement shimming computation. Since a resolution in a circumferential rotation direction differs (the continuously disposed shim trays 14 are present more than the discretely disposed shim trays 11 in the circumferential rotation direction), the number of eigenmodes generally increases in a case of the continuously disposed shim trays 14. Thus, selection of an eigenmode regarding the continuously disposed shim trays 14 is performed by using a number of an eigenmode causing a uniform magnetic field in the circumferential rotation direction as a reference.

Next, in the discrete arrangement shimming computation, calculation regarding "eigenmode intensity computation, eigenmode selection, computation of magnetic body volume required in shimming, and magnetic field prediction after execution of shimming" is performed. The "eigenmode intensity computation" is performed by using Equation (12). FIGS. 10A and 10B are a diagram illustrating that eigenmode intensities (x) are indicated by eigenmode numbers (the sequence of being arranged in the order of magnitude of singular values) with respect to an error magnetic field before shimming. In other words, FIGS. 10A and 10B illustrate that eigenmode intensities are indicated by eigenmodes of two shim trays. The numbers and vertical line segments indicate eigenmodes having a uniform magnetic field distribution in the circumferential rotation direction, and the eigenmodes are fundamental eigenmodes which are important in shimming. Bent lines indicate a maximum-minimum-value width (therefore, homogeneity obtained by being divided by a magnetic field average value) of $B^{res}$ obtained by adding the eigenmodes from the first eigenmode together, and, if an upper limit of the number of eigenmodes is increased, the homogeneity is improved. However, actually, iron pieces cannot be disposed, and thus an upper limit is restricted.

Next, the "eigenmode selection" will be described. In FIGS. 10A and 10B, an eigenmode in which the mark O is added to each eigenmode intensity (x) is a selected eigenmode 15 which is added in magnetic field reconstruction (Equation (13)). An eigenmode with no mark O is an unselected eigenmode 16. Herein, the seventh fundamental eigenmode which is uniform in the circumferential rotation direction is not included, and an eigenmode having a singular value greater than that is selected. If the eigenmode with the mark O is selected, and shimming is performed (that is, magnetic body arrangement in the eigenmode with the mark O is performed), homogeneities on the spherical plane of 45 cm are respectively expected to be 9.13 ppm and 7.55 ppm in FIGS. 10A and 10B. A difference between the homogeneities mainly occurs since a negative iron volume cannot be actually disposed in the discretely disposed shim trays 11 in FIG. 10A, and a negative iron volume of the shim pocket is set to zero. This is derived from the fact that there is also a restriction in a spatial arrangement position. Thus, generally, expectable homogeneity in virtual continuous arrangement shimming computation performed by setting an hCP distribution for the continuously disposed shim trays 14 illustrated in FIG. 10B becomes better. A value better than 7.55 ppm is obtained in the continuously disposed shim trays 14 in FIG. 10B. This homogeneity is a goal in actual shimming.

An iron volume of the shim pocket 5 is obtained within the maximum permissible range in the actual shim pocket 5 so that a magnetic body volume can be set within a restriction in a permissible volume of each shim pocket 5 with respect to an arrangement volume of shimming magnetic bodies regarding the discretely disposed shim trays 11. The following method may be used in order to satisfy such a restriction.

A condition in which a negative iron volume disappears by changing the target magnetic field $B^0_i$.

A negative iron volume is caused not to appear through repetitive computation. A computation value for the shim pocket 5 exceeding the maximum permissible value is caused not to appear.

An eigenmode which partially generates a negative iron volume is permitted.

The above-described conditions take, for example, the following computation procedures.

Shimming computation is performed on an iron volume to be disposed in the discretely disposed shim trays 11 with respect to an error magnetic field.

An iron volume is set to zero in the shim pocket 5 in which a volume of disposed iron is negative. An iron volume of the shim pocket 5 exceeding the maximum value (permissible volume) is set to the maximum permissible volume.

A residual magnetic field is obtained by using a remaining iron volume, and is used to perform the shimming computation 31 again.

The discrete arrangement shimming computation in the above (i), (ii) and (iii) is repeatedly performed several hundred times so that a negative iron volume does not appear. All of a plurality of conditions may be used. FIGS. 11A and 11B illustrate a result of finding a condition causing a negative iron volume to disappear by also using the conditions.

A description will be made of a case where a negative magnetic body volume is caused not to appear by performing repetitive computation during discrete arrangement shimming computation. In first computation of the repetitive computation, a magnetic body volume is computed according to Equation (11), and a magnetic field at a magnetic field evaluation point according to Equation (13). However, there is a case where a negative magnetic body volume is large in the first computation. There is a case where an iron volume of each pocket exceeds the maximum permissible volume of the shim pocket 5. The continuous arrangement shimming computation regarding the continuously disposed shim trays 14 is aimed at being compared with a discrete arrangement shimming computation result regarding the discretely disposed shim trays 11, and thus a negative volume may be present. However, in the discretely disposed shim trays 11, there are an upper limit $V_i^{MX}$ and a lower limit ($V_i^{MN}=0$ in many cases) in a magnetic body volume of each pocket 5. Thus, each element $I_i$ of the vector I in Equation (11) has an upper limit and a lower limit. Therefore, the following expressions are estimated.

$$\text{If } I_i < V_i^{MN}, I_i = V_i^{MN} \tag{15}$$

$$\text{If } I_i > V_i^{MN}, I_i = V_i^{Mx} \tag{16}$$

If a magnetic body volume is defined as a result of the repetitive computation, a magnetic field distribution can be computed. In other words, a new magnetic field to be disposed can be computed according to Equation (3) by using Equation (1) or (2), and Equation (14) is modified as follows.

$$B^{res'} = B^{ER} = B^0 - B^{REC'} \tag{17}$$

Here, the upper script ' indicates a magnetic field corresponding to a restriction of a magnetic body volume in Equations (15) and (16). Here, a new residual magnetic field is a magnetic field which can be said to be an error magnetic field expected to remain after shimming, and, accurately, indicates a magnetic field for which shimming cannot be performed. In other words, the residual magnetic field includes an electromagnetic force generated by a changed iron volume in Equations (15) and (16).

If a magnetic body volume before being changed due to the restriction in Equations (15) and (16) is compared with a magnetic body volume disposed in the shim pocket 5, a vector $I^{ER}$ indicating an error of magnetic body volume arrangement is obtained. Thus, the intensity of an eigenvector is expressed as follows by using Equation (11).

$$P_i^{ER} = \lambda_i v_i I^{ER} / n_p^{1/2}_i \tag{18}$$

Therefore, the generated error magnetic field $B^{ER}$ is expressed by using $I^{ER}$.

$$B^{ER} = \Sigma n_p^{1/2} P_i^{ER} u_i \tag{19}$$

However, in the shimming method of the present embodiment, since discrete arrangement shimming computation can be performed on the error magnetic field again, the next magnetic body volume is computed by using Equations (11), (12) and (13), and the restrictions in Equations (15) and (16) are set again. Thereafter, an error magnetic field is computed according to Equation (17) again. If there is no magnetic body volume exceeding the restrictions in Equations (15) and (16), repetitive computation here is finished. However, in a case where a volume deviated from the magnetic body volume is calculated according to Equation (11), an error magnetic field is further computed according to Equation (19), and a magnetic body volume is computed again.

For eigenmodes of the eigenmode number $M_D$ or less, already selected in a new error magnetic field generated according to Equation (19), computation using Equation (11) is performed so that an intensity thereof becomes zero. However, the error magnetic field obtained according to Equation (19) is also generated for the unselected eigenmode 16. In other words, this indicates that a new error magnetic field component is generated in Equations (15) and (16) in eigenmodes having numbers of the eigenmode number $M_D$ or more and small singular values. However, an error magnetic field generated in the eigenmodes having small singular values is slight (an eigenmode intensity tends to have a very small value), and thus scarcely influences a magnetic field after new shimming. As a result, magnetic bodies can be disposed in the shim pockets 5 of the discretely disposed shim trays 11 in an arrangement volume within a restriction in the homogeneity of a magnetic field after shimming.

In the illustrated example, eigenmode intensities of below No. 97 are almost zero in an expected residual magnetic field after shimming, and do not appear in FIG. 11A. Here, FIGS. 11A and 11B illustrate that eigenmode intensities are indicated by eigenmodes of two shim trays. In other words, FIG. 11B is the same as FIG. 10B, and illustrates eigenmodes of an error magnetic field before shimming. Homogeneities after shimming in FIGS. 11A and 11B are written on upper parts, and are respectively 7.52 and 7.31 ppm. A difference between both of the two homogeneities is smaller than in FIGS. 10A and 10B, and thus it can be seen that a condition under which shimming close to a case of the continuously disposed shim trays 14 can be performed is retrieved in the discretely disposed shim trays 11. In other words, it can be said that an error magnetic field of a high-order component generated by operating Equations (15) and (16) is slight.

In FIGS. 11A and 11B, compared with FIGS. 10A and 10B, a target magnetic field is set to be reduced from 1.5012 to 1.500947 T as illustrated on the upper part in the figure. Regarding numerical values it is determined on the upper part, the maximum and minimum values of an error magnetic field before shimming illustrated on an upper side, and the maximum and minimum values of an error magnetic field after shimming illustrated on a lower side are indicated by homogeneities and maximum and minimum magnetic field intensity values. Generally, an iron piece absorbs a magnetic flux, and thus weakens a magnetic field in the system of the MRI magnet as illustrated in FIGS. 3A and 3B.

Thus, a magnetic field is slightly reduced. In the same manner as in a case of FIGS. 10A and 10B, in eigenmode selection during shimming, the seventh fundamental eigenmode which is uniform in the circumferential rotation direction is not included, and fundamental eigenmodes (smaller numbers) greater than that are included. The exactly same condition is given in the continuously disposed shim trays 14, but, in the discretely disposed shim trays 11, repetitive computation which is performed until a negative volume completely disappears is not performed on eigenmodes interposed between two vertical lines extending vertically from the X axis and including No. 1 eigenmode which is uniform in the circumferential rotation direction. Such eigenmodes are included at the beginning of repetitive computation, and iron pieces for reducing the eigenmode intensity are disposed in the shim pocket 5 of a positive volume. Thus, in a case of FIGS. 10A and 10B, it can be seen that the eigenmode intensity is lower than in an error magnetic field before shimming.

On the other hand, a magnetic body volume increases for a high-order eigenmode having a small singular value. Thus, it is difficult to determine a magnetic body volume within a restriction in the shim pocket 5 in repetitive computation during shimming computation described in Equations (15) to (19). In such high-order components, the restrictions in Equations (15) and (16) are applied to an iron volume, but the repetitive computation during shimming computation may be stopped even if an iron volume is not included in the restrictions.

In the example illustrated in FIGS. 11A and 11B, since this computation method is applied to eigenmodes from. No. 97 to below No. 121 (between the two vertical lines; eigenmode numbers are described in eigenmodes in discrete arrangement), intensities of the eigenmodes are not zero. Among the eigenmodes in FIGS. 11A and 11B, an eigenmode indicated by a vertical end short line segment and a number is an eigenmode component (fundamental eigenmodes) which is uniform in the circumferential rotation direction and is symmetric in the axial direction (hereinafter, simply referred to as uniform in the circumferential rotation direction). In a magnet of this computation example, the number of coil blocks of main coils mainly forming a static magnetic field in an imaging region in a tunnel type MRI apparatus is assumed to be six, and, with respect thereto, this computation method is applied to the sixth and seventh eigenmodes of the eigenmodes which are uniform in the circumferential rotation direction, and repetitive computation is not applied thereto. In FIGS. 11A and 11B, the computation method is applied to the vicinity of the sixth eigenmode which is uniform in the circumferential rotation direction, and thus intensities of eigenmodes corresponding to eigenmode numbers present around this fundamental eigenmode are not zero.

Thus, compared with a case of the continuously disposed shim trays 14 in FIG. 11B, to which repetitive computation is not applied, the intensity is not completely zero, but it can be seen that the intensity is reduced according to the shimming computation of the present method.

In the "computation of iron volume required in shimming", as illustrated in FIGS. 11A and 11B, an iron volume is acquired while performing the above-described repetitive computation in the selected eigenmode. FIG. 12 illustrates a shimming iron volume which is actually disposed in the discretely disposed shim pockets. FIG. 12 is a diagram illustrating iron piece volumes of the shim tray pockets and a current potential distribution of the continuously disposed shim trays. Each shim pocket 5 is indicated by a rectangle, and a shimming iron volume disposed in the pocket is indicated by a numerical value (herein, the unit thereof is cubic cm or cc).

In this figure, a position in the circumferential rotation direction is indicated by an angle, a longitudinal axis expresses a position in the axial direction, and the apparatus center is indicated as zero. During actual shimming work, a shimming iron volume may be output in numerical values separately from this figure, and may be displayed on a screen or may be printed for each pocket number. In this figure, the contour line is a contour line of a virtual current potential computed for the continuously disposed shim trays 14. In addition, hCP is permitted to be even negative, and a negative volume is allocated to a spot region. An upper part in the figure illustrates expected values of a shimming result. The uppermost row of three rows describes a size of a cylindrical surface on which the shim pockets 5 are disposed, that is, a radius (m) and an axis length (m). The next row describes a homogeneity expected value (ppm) after shimming, a target magnetic field (T), a total volume (cc) of disposed iron pieces, and a size of each shim pocket 5 in the unit of m. The next row describes homogeneity (ppm) before shimming, a contour line interval (A) of a virtual current potential (hCP) distribution, maximum and minimum values (cc) of iron volumes disposed in the shim pocket 5, and the arrangement unit (m) of the respective pockets.

Regarding iron pieces disposed in the shim pocket 5, it is not possible to dispose an iron sheet having a thickness of several sheets, that is, a standardized iron sheet, and thus to dispose iron pieces having a continuous thickness (any numerical value is freely employed). In this case, iron pieces do not have a resolution in a sheet thickness of the minimum thickness or less, and thus a disposed iron piece volume have a discrete value. Therefore, a residual of an iron volume of the minimum unit or less is approximately rounded off, and thus influences an error magnetic field. In order to minimize this, shimming conditions (the number of eigenmodes or a target magnetic field intensity) are determined. The homogeneity expected value in FIGS. 11A and 11B is a value in which discretization of an iron piece volume is taken into consideration.

If arrangement of a shimming iron volume is defined, the "magnetic field prediction after execution of shimming" can be performed as follows.

$$B^{SM} = B^{FE}(I) + B^{MG} \qquad (20)$$

Here, $B^{SM}$ indicates a magnetic field distribution computation value after the present shimming, $B^{FE}(I)$ indicates a magnetic field distribution caused by iron piece arrangement, and $B^{MG}$ indicates a measured magnetic field distribution. The shimming work is repeatedly performed several times, and thus these computation and measurement are performed every time so that the magnetic field distribution $B^{SM}$ after shimming is estimated.

FIG. 13 is a diagram illustrating a magnetic field intensity distribution after shimming on a plane of Y=0 as a distribution on a plane of an axial direction position Z and a horizontal direction position X (refer to FIG. 5 with respect to coordinates). In the figure, a spot region is a region in which a magnetic field $B_i^{SM}$ after shimming, exceeding a target magnetic field (herein, 1.5 T) is expected through shimming computation. A radial line is a contour line 18 of ±1 ppm (1.5 μT) with respect to the target magnetic field. Of the two circles, an outer circle indicates a spherical plane with 50 cm on which magnetic field measurement is performed, and an inner circle indicates a spherical plane with 40 cm close to an elliptical plane (having a diameter of 40 cm and a width of 37 cm in the axial direction on an X-Y plane) on which magnetic field evaluation points are disposed through shimming computation. In the example of the shimming computation, a magnet having six main coils is used, a region in which a magnetic field is expected to be high is generated so as to correspond to a coil block of the main coils, and thus a magnetic field distribution shown in a document can be reproduced through shimming. In other words, as illustrated in FIGS. 11A and 11B, this indicates that an error magnetic field component corresponding to a low-order eigenmode is canceled through shimming, and only a high-order component of an inherent magnetic field component remains as a residual magnetic field.

As mentioned above, if the discrete arrangement shimming computation and the continuous arrangement shimming computation are completed, a shimming iron volume and a magnetic field distribution after shimming are determined. In FIG. 17, this corresponds to a portion "magnetic field evaluation after shimming and evaluation of an iron volume required in shimming (S205)". If this is not appropriate, shimming computation is performed again. In this case, discrete arrangement shimming computation and continuous arrangement shimming computation are performed by selecting a target magnetic field intensity and an eigenmode used for shimming, and examining changes of a weight of the shim pocket 5 and a magnetic field evaluation position. This is performed until appropriate shimming computation is performed, that is, only an appropriate error magnetic field remains, and an arrangement volume of shimming magnetic bodies included in an arrangement restriction volume of the shim pocket 5 is obtained.

If a result of the shimming computation is appropriate, the flow returns to the processes of actually disposing iron pieces in the shim pockets 5 (shimming work (S05)), measuring a magnetic field again (S02), and performing magnetic field interpolation/extrapolation computation (S201) and evaluating homogeneity (S202). The repetitive shimming work including magnetic field measurement, shimming support computation, magnetic body (iron piece) arrangement, and magnetic field measurement is repeatedly performed until a magnetic field satisfying the specification is obtained.

Example 2

As Example 2, a magnetic body volume and a magnetic moment distribution obtained as a result of shimming computation are increased. This Example is combined with Example 1 and is used, and is thus illustrated in FIG. 12. The content as illustrated in FIG. 12 is displayed on the display unit 107, and thus it is possible to improve shimming work efficiency of a worker. The content displayed on the display unit 107 may be changed as appropriate according to the worker's request or the work content. For example, if there is a request for the magnitude of an eigenmode intensity and the extent of reduction in an error magnetic field as illustrated in FIGS. 10 and 11 to be desired to be visually recognized, this content may be displayed on the display unit 107.

In FIG. 12, the contour line is a contour line regarding a virtual current potential, and indicates a magnetic moment (magnetic moment density) distribution (Am$^2$/m$^2$) per unit area in a case of continuous arrangement. On the other hand, the spot region is a region of a negative virtual current potential (hCP). In computation of hCP, repetitive computation in shimming computation using only a positive value is not performed, and thus a negative hCP is present. However, if compared with a numerical value of an iron piece volume, it can be seen that the iron piece volume is also reduced, and thus there is no contradiction between two arrangements, in the region of hCP<0. As a result, the entire image of iron piece arrangement is easily recognized. In the figure, the contour line extends horizontally as a whole, and thus it can be seen that there is no biased error magnetic field as a whole.

FIG. 14 is a diagram illustrating a relationship between eigenmodes based on discrete arrangement and eigenmodes based on continuous arrangement. FIG. 14 illustrates a relationship between eigenmodes for two kinds of the shim trays 11 and 14. An inner product between both of the two trays is obtained as follows, and an inner product value is spotted for $S_{ij}$<0.5.

$$S_{ij} = uD_i \cdot uC_j \quad (21)$$

The discretely disposed shim trays 11 are disposed in twelve axial directions in the circumferential rotation direction as in FIG. 12. A bent line indicates $g_i$ (reproduction ratio), that is, to what extent $uD_i$ of the eigenmodes based on the discretely disposed shim trays on a longitudinal axis can be reproduced by $uC$ of the eigenmodes based on the continuously disposed shim trays, by using a reproduction index (%) of an i-th discretely disposed shim tray eigenmode. This is computed as follows.

$$g_j = 100\{\Sigma(uD_j \cdot uC_k)^2\}^{1/2} \quad (22)$$

Here, summation is performed according to eigenmode numbers based on the k continuously disposed shim trays 14. In other words, comparison between both of the two trays indicates deterioration in magnetic field reproducibility in magnetic bodies disposed in the shim trays when conditions to be imposed on computation are changed from continuous arrangement to discrete arrangement. A numerical value in the figure indicates a fundamental eigenmode which is uniform in the circumferential rotation direction, and indicates a number added to the fundamental eigenmode in the order of magnitude of a singular value.

It can be seen that there is the presence of an eigenmode of the continuously disposed shim trays 14 in which $g_j$ in Equation (22) becomes zero if the sixth fundamental eigenmode which is uniform in the circumferential rotation direction is exceeded. In other words, in arrangement of twelve (circumferential rotation) x twenty-four (axial direction), it can be said that magnetic fields up to sixth fundamental eigenmode which is uniform in the circumferential rotation direction can be reproduced. A typical MRI magnet has six coil blocks of main coils, and, actually, a magnetic body volume to be disposed is considerably increased in an eigenmode which is uniform in the seventh circumferential rotation direction, and thus shimming cannot be performed. In this meaning, it can be said that the 12×24 discretely disposed shim trays 11 in which shimming can be performed in fundamental eigenmodes which are uniform up to the sixth circumferential rotation direction have arrangement in which shimming can be sufficiently performed.

Conversely, if this examination is used, the validity of design of the discretely disposed shim trays 11 can be checked, and thus the validity of design of shim trays suitable for an actual apparatus can be checked. In other words, in a case where shim trays are designed, but only eigenmodes in which reproducibility of a magnetic field in eigenmodes for continuously disposed shim trays is low are obtained, it can be seen that the discretely disposed shim trays are required to be designed again.

Hitherto, the magnet system including the magnet apparatus forming a uniform magnetic field intensity distribution in a predetermined space and the shim trays as a mechanism correcting a magnetic field intensity distribution is assumed, and a description has been made of the shimming method (magnetic field adjusting method) of the present embodiment assuming a case where shimming magnetic bodies (iron in the above description) are disposed in the shim trays.

However, an embodiment of the present invention is not limited thereto, and may be freely changed as long as the spirit of the invention is not changed. For example, as a magnetic field measurement mechanism, a shim coil may be used instead of a shim tray and a shimming magnetic body. In this case, the magnitude of magnetic moment generated by the shim coil is computed as an adjustment target. A shimming magnetic body is not limited to iron, and a member in which magnetic moment when saturated and magnetized is constant with high accuracy may be used as necessary. A shim tray is not strictly limited to a tray shape, and it is clear that, if a shim tray has a structure in which a shimming magnetic body can be disposed therein, the shim tray may be used.

REFERENCE SIGNS LIST

1 VIRTUAL CURRENT PLANE
2 MAGNETIC FIELD EVALUATION PLANE

3 CONTINUOUSLY DISPOSED SHIM TRAY
4 IMAGING REGION (FOV)
5 SHIM POCKET OF DISCRETELY DISPOSED SHIM TRAY
6 MAGNETIC FIELD PP VALUE INDICATED BY FUNCTION OF EIGENMODE UPPER LIMIT
7 ERROR MAGNETIC FIELD INTENSITY CONTOUR LINE
8 MAGNETIC FIELD MEASUREMENT PLANE
9 NUMBER POSITION OF AXIALLY SYMMETRIC EIGENMODE
10 MRI MAGNET
10f BORE OF MRI MAGNET
11 DISCRETELY DISPOSED SHIM TRAY
15 EIGENMODE (SELECTED)
16 EIGENMODE (UNSELECTED)
17 EXPECTED REACHABLE HOMOGENEITY
18 RESIDUAL MAGNETIC FIELD CONTOUR LINE (±1 PPM)
20 MAGNETIC SENSOR SUPPORT PLATE
22 SUBJECT
23 BED
24 GRADIENT MAGNETIC FIELD COIL

The invention claimed is:

1. A magnetic field adjusting method of correcting a magnetic field distribution generated by a magnet apparatus by disposing a shimming magnetic body in a shim tray in a magnet system including the magnet apparatus forming a uniform magnetic field intensity distribution in a predetermined space and the shim tray correcting the magnetic field intensity distribution, the method comprising:
   a first step of measuring a magnetic field intensity distribution on a predefined closed curved plane;
   a second step of acquiring an error magnetic field distribution which is a difference between the magnetic field intensity distribution acquired in the first step and a target magnetic field intensity distribution;
   a third step of computing an arrangement condition of a shimming magnetic body forming a correction magnetic field distribution for reducing the error magnetic field distribution under a quantitatively continuous numerical value condition;
   a fourth step of computing an arrangement condition of a shimming magnetic body forming a correction magnetic field distribution for reducing the error magnetic field distribution under a spatially and quantitatively discrete numerical value condition;
   a fifth step of adding a correction magnetic field formed by the shimming magnetic body disposed on the basis of the arrangement condition acquired in the third step to the measured magnetic field intensity distribution so as to obtain a magnetic field intensity distribution after first correction;
   a sixth step of adding a correction magnetic field formed by the shimming magnetic body disposed on the basis of the arrangement condition acquired in the fourth step to the measured magnetic field intensity distribution so as to obtain a magnetic field intensity distribution after second correction; and
   a seventh step of obtaining a difference between the magnetic field intensity distribution after the first correction and the magnetic field intensity distribution after the second correction, changing the predetermined space or the target magnetic field intensity distribution in a case where the difference is equal to or more than a predefined predetermined threshold value so that computation is performed again from the second step, and disposing the shimming magnetic body in the shim tray according to the arrangement condition acquired in the fourth step in a case where the difference is less than the predefined predetermined threshold value.

2. The magnetic field adjusting method according to claim 1,
   wherein, in the second step,
   a magnetic field intensity distribution on a magnetic field measurement plane included in the closed curved plane is estimated, and
   a difference between the estimated magnetic field intensity distribution and the target magnetic field intensity distribution is acquired as the error magnetic field intensity distribution.

3. The magnetic field adjusting method according to claim 1,
   wherein, in computation of the arrangement condition of the shimming magnetic body in the third step and the fourth step,
   a magnetic body distribution or a magnetic moment distribution causing a necessary correction magnetic field of an error magnetic field distribution to be approximately generated is obtained by using a regularization method using truncated singular value decomposition in a linear equation system formed of the correction magnetic field, a volume of shimming magnetic bodies to be disposed and magnetic moment to be disposed, and a response matrix to the correction magnetic field from the volume of shimming magnetic bodies to be disposed or the magnetic moment to be disposed.

4. The magnetic field adjusting method according to claim 1,
   wherein, in the third step and the fourth step,
   an eigenmode indicating a one-to-one relationship between a magnetic body volume to be disposed or magnetic moment, and a magnetic field distribution formed by the magnetic body volume to be disposed or the magnetic moment is obtained, and eigenmodes of a predetermined number are selected from among the eigenmodes whose intensities are the maximum and are added together so that an arrangement distribution of shimming magnetic bodies is obtained.

5. The magnetic field adjusting method according to claim 4,
   wherein the eigenmodes are calculated according to singular value decomposition, and are organized in the order of greater singular values acquired according to the singular value decomposition, and
   wherein an eigenmode intensity is acquired through an inner product between an eigen magnetic field distribution and the error magnetic field distribution with respect to each of the plurality of eigenmodes.

6. The magnetic field adjusting method according to claim 1,
   wherein, in the seventh step, the shimming magnetic body is disposed in the shim tray, and then the first step to the seventh step are performed.

7. The magnetic field adjusting method according to claim 4,
   wherein the magnetic field intensity distribution after the first correction and the magnetic field intensity distribution after the second correction are obtained as a function of the number of eigenmodes which are added together, and
   wherein the magnitude of a residual magnetic field which is a difference between the magnetic field intensity distribution after the first correction and the magnetic field intensity distribution after the second correction, and the target magnetic field is acquired as a peak-to-peak value of residual magnetic field or a volume root-mean-square residual magnetic field.

8. The magnetic field adjusting method according to claim 1,
wherein the magnetic field evaluation plane is disposed on a spherical plane, an elliptical plane, or a cylindrical plane, and
wherein the second step to the seventh step are performed on a magnetic field intensity distribution on the magnetic field evaluation plane.

9. The magnetic field adjusting method according to claim 1,
wherein, in the second step,
a virtual current potential plane which includes the closed curved plane in the first step and to which a current potential approximately reproducing the measured magnetic field intensity distribution is allocated is virtually disposed,
a magnetic field intensity distribution on the magnetic field evaluation plane is estimated from the virtual current potential plane, and
a difference between the target magnetic field intensity distribution and the estimated magnetic field intensity distribution on the magnetic field evaluation plane is acquired as the error magnetic field intensity distribution.

10. The magnetic field adjusting method according to claim 9,
wherein the magnetic field evaluation plane is changed, and an error magnetic field distribution on the changed magnetic field evaluation plane is adjusted.

11. The magnetic field adjusting method according to claim 9,
wherein a current potential on the virtual current potential plane is decomposed into a virtual current potential distribution in which a magnetic moment direction is directed in a magnetic field direction, and an eigenmode of a magnetic field distribution by using truncated singular value decomposition, so that an eigenmode intensity in each eigenmode is specified,
wherein approximate accuracy of a measured magnetic field is added from a first eigenmode in the order of singular values so as to be specified as a function of an upper limit eigenmode number, and
wherein an eigenmode upper limit and a current plane are selected so that a magnetic field evaluation error is less than a permissible value of a target residual magnetic field after shimming.

12. The magnetic field adjusting method according to claim 2,
wherein, the arrangement condition of the shimming magnetic body forming a correction magnetic field distribution in the fourth step includes
setting in advance the maximum value and the minimum value of a permissible magnetic body volume of a shim pocket in which a shimming magnetic body is to be disposed,
setting a magnetic body volume of a pocket exceeding the maximum value as a magnetic body volume of which the maximum value is to be disposed, and
setting a magnetic body volume of a pocket less than the minimum value as a magnetic body volume of which the minimum value is to be disposed, correcting a magnetic field at an magnetic field evaluation point through computation on the basis of a measured magnetic field by using a magnetic field based on the set magnetic body volume, repeatedly performing computation of a shimming magnetic body volume and correction of the maximum and minimum values of a magnetic body volume to be disposed with respect to the corrected magnetic field at the magnetic field evaluation point, and repeatedly performing computation in the step 4 in which a magnetic body volume to be disposed in the shim pocket is included in a permissible magnetic body volume.

13. The magnetic field adjusting method according to claim 12, further comprising:
a step of adding a weight to the shim pocket in repetitive computation in the step 4 until a magnetic body volume included in a permissible magnetic body volume of the shim pocket is calculated.

14. The magnetic field adjusting method according to claim 1, further comprising:
a step of discretizing a shimming magnetic body volume to be disposed on the basis of a unit iron volume set in advance as a quantitative arrangement condition in the third step, and presenting a corrected magnetic field distribution and homogeneity which are calculation results in the fifth step and the seventh step using the discretized magnetic body volume.

15. The magnetic field adjusting method according to claim 14, further comprising:
a computation process of presenting a distribution of an error magnetic field due to the discretization of a shimming magnetic body volume in the third step, and an eigenmode intensity of the error magnetic field, and changing an upper limit eigenmode or a target magnetic field intensity in shimming computation so that the error magnetic field is reduced.

16. The magnetic field adjusting method according to claim 15, further comprising:
a computation process of comparing results of shimming computation using a shim pocket based on discrete arrangement and shimming computation based on continuous arrangement with each other, and changing an upper limit eigenmode or a target magnetic field intensity in the shimming computation so that the error magnetic field is reduced.

17. The magnetic field adjusting method according to claim 2,
wherein, in computation of the arrangement condition of the shimming magnetic body in the third step and the fourth step,
a magnetic body distribution or a magnetic moment distribution causing a necessary correction magnetic field of an error magnetic field distribution to be approximately generated is obtained by using a regularization method using truncated singular value decomposition in a linear equation system formed of the correction magnetic field, a volume of shimming magnetic bodies to be disposed and magnetic moment to be disposed, and a response matrix to the correction magnetic field from the volume of shimming magnetic bodies to be disposed or the magnetic moment to be disposed.

18. The magnetic field adjusting method according to claim 2,
wherein, in the third step and the fourth step,
an eigenmode indicating a one-to-one relationship between a magnetic body volume to be disposed or magnetic moment, and a magnetic field distribution formed by the magnetic body volume to be disposed or the magnetic moment is obtained, and eigenmodes of a predetermined number are selected from among the eigenmodes whose intensities are the maximum and are added together so that an arrangement distribution of shimming magnetic bodies is obtained.

19. The magnetic field adjusting method according to claim 2,
wherein, in the seventh step, the shimming magnetic body is disposed in the shim tray, and then the first step to the seventh step are performed.

20. The magnetic field adjusting method according to claim 2,
wherein the magnetic field evaluation plane is disposed on a spherical plane, an elliptical plane, or a cylindrical plane, and
wherein the second step to the seventh step are performed on a magnetic field intensity distribution on the magnetic field evaluation plane.

21. The magnetic field adjusting method according to claim 2,
wherein, in the second step,
a virtual current potential plane which includes the closed curved plane in the first step and to which a current potential approximately reproducing the measured magnetic field intensity distribution is allocated is virtually disposed,
a magnetic field intensity distribution on the magnetic field evaluation plane is estimated from the virtual current potential plane, and
a difference between the target magnetic field intensity distribution and the estimated magnetic field intensity distribution on the magnetic field evaluation plane is acquired as the error magnetic field intensity distribution.

22. The magnetic field adjusting method according to claim 2, further comprising:
a step of discretizing a shimming magnetic body volume to be disposed on the basis of a unit iron volume set in advance as a quantitative arrangement condition in the third step, and presenting a corrected magnetic field distribution and homogeneity which are calculation results in the fifth step and the seventh step using the discretized magnetic body volume.

* * * * *